United States Patent [19]
Cochrane et al.

[11] Patent Number: 5,789,381
[45] Date of Patent: Aug. 4, 1998

[54] PULMONARY SURFACTANT PROTEINS AND RELATED POLYPEPTIDES

[75] Inventors: Charles G. Cochrane, La Jolla; Susan D. Revak, San Diego, both of Calif.

[73] Assignee: The Scripps Research Institute, La Jolla, Calif.

[21] Appl. No.: 419,824

[22] Filed: Apr. 11, 1995

Related U.S. Application Data

[63] Continuation of Ser. No. 60,833, May 12, 1993, Pat. No. 5,407,914, which is a continuation-in-part of Ser. No. 715, 397, Jun. 14, 1991, Pat. No. 5,260,273, which is a continuation-in-part of Ser. No. 293,201, Jan. 4, 1989, Pat. No. 5,164,369, which is a continuation-in-part of Ser. No. 141, 200, Jan. 6, 1988, abandoned.

[51] Int. Cl.$^6$ .................................................. A61K 38/16
[52] U.S. Cl. ........................ 514/13; 424/450; 530/326
[58] Field of Search .................... 514/2, 15, 14, 514/13, 12; 530/324, 326, 327, 328; 424/450

[56] References Cited

U.S. PATENT DOCUMENTS

| | | | |
|---|---|---|---|
| 4,562,003 | 12/1985 | Lewicki | 435/68 |
| 4,643,988 | 2/1987 | Segrest et al. | 514/12 |
| 4,656,253 | 4/1987 | Lewicki | 436/548 |
| 4,861,756 | 8/1989 | Jackson | 514/11 |
| 5,164,369 | 11/1992 | Cochrane et al. | 514/12 |
| 5,260,273 | 11/1993 | Cochrane et al. | 514/12 |
| 5,407,914 | 4/1995 | Cochrane et al. | 514/12 |

*Primary Examiner*—Cecilia J. Tsang
*Assistant Examiner*—Patrick R. Delaney
*Attorney, Agent, or Firm*—Olson & Hierl, Ltd.

[57] ABSTRACT

The present invention discloses useful peptides and synthetic pulmonary surfactants, as well as methods of making and using same. In one preferred embodiment, a synthetic pulmonary surfactant comprises one or more pharmaceutically acceptable phospholipids admixed with a polypeptide comprising at least 10 amino acid residues and no more than about 60 amino acid residues, said polypeptide including a sequence having alternating hydrophobic and hydrophilic amino acid residue regions. In other embodiments, a surfactant peptide has an amino acid residue sequence selected from the group consisting of KLLLLKLLLLKLLLLKLLLK, KLLLLLLLKLLLLLLLKLL, and KKLLLLLLKKLLLLLLKKL.

6 Claims, 8 Drawing Sheets

```
CAC CTG GGC CTG TGC AAA TCC CGG CAG CCA GAG CCA GAG CAG GAG        45
His Leu Gly Leu Cys Lys Ser Arg Gln Pro Glu Pro Glu Gln Glu
-62

CCA GGG ATG TCA GAC CCC CTG CCC AAA CCT CTG CGG GAC CCT CTG        90
Pro Gly Met Ser Asp Pro Leu Pro Lys Pro Leu Arg Asp Pro Leu

CCA GAC CCT CTG CTG GAC AAG CTC GTC GTC CCT GTG CTG CCC GGG       135
Pro Asp Pro Leu Leu Asp Lys Leu Val Val Pro Val Leu Pro Gly

GCC CTC CAG GCG AGG CCT GGG CCT CAC ACA CAG GAT CTC TCC GAG       180
Ala Leu Gln Ala Arg Pro Gly Pro His Thr Gln Asp Leu Ser Glu

CAG CAA TTC CCC ATT CCT CTC CCC TAT TGC TGG CTC TGC AGG GCT       225
Gln Gln Phe Pro Ile Pro Leu Pro Tyr Cys Trp Leu Cys Arg Ala
    -1  1

CTG ATC AAG CGG ATC CAA GCC ATG ATT CCC AAG GGT GCG CTA GCT       270
Leu Ile Lys Arg Ile Gln Ala Met Ile Pro Lys Gly Ala Leu Ala

GTG GCA GTG GCC CAG GTG TGC CGC GTG GTA CCT CTG GTG GCG GGC       315
Val Ala Val Ala Gln Val Cys Arg Val Val Pro Leu Val Ala Gly

GGC ATC TGC CAG TGC CTG GCT GAG CGC TAC TCC GTC ATC CTG CTC       360
Gly Ile Cys Gln Cys Leu Ala Glu Arg Tyr Ser Val Ile Leu Leu

GAC ACG CTG CTG GGC CGC ATG CTG CCC CAG CTG GTC TGC CGC CTC       405
Asp Thr Leu Leu Gly Arg Met Leu Pro Gln Leu Val Cys Arg Leu

GTC CTC CGG TGC TCC ATG GAT GAC AGC GCT GGC CCA AGG TCG CCG       450
Val Leu Arg Cys Ser Met Asp Asp Ser Ala Gly Pro Arg Ser Pro
                        81

ACA GGA GAA TGG CTG CCG CGA GAC TCT GAG TGC CAC CTC TGC ATG       495
Thr Gly Glu Trp Leu Pro Arg Asp Ser Glu Cys His Leu Cys Met

TCC GTG ACC ACC CAG GCC GGG AAC AGC AGC GAG CAG GCC ATA CCA       540
Ser Val Thr Thr Gln Ala Gly Asn Ser Ser Glu Gln Ala Ile Pro
                        110

CAG GCA ATG CTC CAG GCC TGT GTT GGC TCC TGG CTG GAC AGG GAA       585
Gln Ala Met Leu Gln Ala Cys Val Gly Ser Trp Leu Asp Arg Glu

AAG TGC AAG CAA TTT GTG GAG CAG CAC ACG CCC CAG CTG CTG ACC       630
Lys Cys Lys Gln Phe Val Glu Gln His Thr Pro Gln Leu Leu Thr

CTG GTG CCC AGG GGC TGG GAT GCC CAC ACC ACC TGC CAG GCC CTC       675
Leu Val Pro Arg Gly Trp Asp Ala His Thr Thr Cys Gln Ala Leu

GGA GTG TGT GGG ACC ATG TCC AGC CCT CTC CAG TGT ATC CAC AGC       720
Gly Val Cys Gly Thr Met Ser Ser Pro Leu Gln Cys Ile His Ser

CCC GAC CTT TGATGAGAAC TCAGCTGTCCA                                 750
Pro Asp Leu
        181
```

FIG. 1

PULMONARY SURFACTANT PROTEINS AND RELATED POLYPEPTIDES

CROSS REFERENCE TO RELATED APPLICATIONS

This is a continuation of application Ser. No. 08/060,833, filed May 12, 1993 now U.S. Pat. No. 5,407,914, which is a continuation-in-part of application Ser. No. 07/715,397, filed Jun. 14, 1991 (now U.S. Pat. No. 5,260,273), which is a continuation-in-part of application Ser. No. 07/293,201, filed Jan. 4, 1989 (now U.S. Pat. No. 5,164,369), which is a continuation-in-part of application Ser. No. 141,200, filed Jan. 6, 1988 (now abandoned), the disclosures of which are hereby incorporated by reference.

TECHNICAL FIELD

The present invention relates to SP18 monomer-related polypeptides useful in forming synthetic pulmonary surfactants. The present invention also relates to a recombinant nucleic acid molecule carrying a structural gene that encodes human SP18 monomer protein and the use of such a recombinant molecule to produce human SP18 monomer.

BACKGROUND

Pulmonary surfactant (PS) lines the alveolar epithelium of mature mammalian lungs. Natural PS has been described as a "lipoprotein complex" because it contains both phospholipids and apoproteins that interact to reduce surface tension at the lung air-liquid interface.

Since the discovery of pulmonary surfactant, and the subsequent finding that its deficiency is a primary cause of neonatal and adult respiratory distress syndrome (RDS), a number of studies have been directed towards developing effective surfactant replacement therapy for affected individuals, particularly infants, using exogenous PS. For instance, improvements in lung function as measured by a decrease in mean airway pressure and oxygen requirements have been demonstrated using exogenous surfactants in human pre-term infants. See Hallman, et al, *Pediatrics* 71: 473–482 (1983); Merritt, et al, *J. Pediatr.* 108: 741–745 (1986); Hallman, et al, *J. Pediatr.* 106: 963–969 (1985); Morley, et al, *Lancet* 1: 64–68 (1981); Merritt, et al, *New England J. Med.* 315: 785–790 (1986), Smyth, et al, *Pediatrics* 71: 913–917 (1983); Enhorning, et al, *Pediatrics* 76: 145–153 (1985); Fujiwara, et al, *The Lancet* 1: 55–59 (1980); Kwong, et al, *Pediatrics* 76: 585–592 (1985); Shapiro, et al, *Pediatrics* 76: 593–599 (1985); Fujiwara, in "Pulmonary Surfactant", Robertson, B., Van Golde, L.M.G., Batenburg J. (eds), Elsevier Science Publishers, Amsterdam, pp. 479–503, (1984).

From a pharmacologic point of view, the optimal exogenous PS to use in the treatment of RDS would be one completely synthesized in the laboratory, under controlled and sterile conditions, with negligible batch-to-batch variability in properties. To minimize the possibility of immunologic complications, the apoprotein component of an exogenous PS should be identical to that found in humans. Unfortunately, the composition of naturally occurring PS is complex, and the art has not yet identified all of the biochemical components that generate the biophysical properties needed for high physiologic activity in lungs. In particular, the art has failed to characterize all of the apoproteins present in natural PS or identify the function of the PS apoproteins presently known.

It should be noted that the literature on PS apoproteins and their roles in surfactant function is complex, inconsistent and sometimes contradictory because heterogenous apoprotein preparations were used in many studies. To date, the art has not definitively established the number of different apoproteins present in natural PS.

Of particular interest to the present invention is the use of a low molecular weight (LMW) human PS-associated apoprotein as a component in an exogenous surfactant. Several studies have attempted to isolated or define human PS LMW apoproteins using biochemical techniques. See, for example, Phizackerley, et al, *Biochem. J.* 183: 731–736 (1979), Revak, et al, *Am. Rev. Resp. Dis.* 134: 1258–1265 (1986), Suzuki, et al, *Eur. J. Respir. Dis.* 69: 335–345 (1986), Taeusch, et al, *Pediatrics* 77: 572–581 (1986), Yu, et al, *Biochem. J.* 236: 85–89 (1986), Whitsett, et al, *Pediatric Res.* 20: 460–467 (1986), Whitsett, et al, *Pediatric Res.* 20: 744–749 (1986), Takahashi, et al, *Biochem. Biophys. Res. Comm.* 135: 527–532 (1986), Suzuki, et al, *Exp. Lung. Res.* 11: 61–73 (1986), Curstedt, et al, *Eur. J. Biochem.* 168: 255–262 (1987), Notter, et al, *Chem. Phys. Lipids* 44: 1–17 (1987), and Phelps, et al, *Am. Rev. Respir. Dis.* 135: 1112–1117 (1987).

Recently, the art has begun to apply the methods of recombinant DNA technology to overcome the problems associated with not being able to isolate to homogeneity the individual LMW PS apoproteins. For instance, Glasser, et al, *Proc. Nat. Acad. Sci. USA* 84: 4007–4011 (1987) reported a cDNA derived sequence of amino acid residues that forms at least a portion of a human precursor protein from which at least one mature LMW apoprotein, which they designated SPL (Phe), is formed. While Glasser, et al. were not able to determine the carboxy-terminal residue of SPL(Phe), and therefore were not able to identify its complete sequence, they did predict that mature SPL(Phe) was about 60 amino acids in length.

Jacobs, et al, *J. Biol. Chem.* 262: 9808–9811 (1987) have described a cDNA and derived amino acid residue sequence for a human precursor protein similar to that described by Glasser, et al. supra. However, according to Jacobs et al. the mature LMW apoprotein, which they designated PSP-B, formed from the precursor would be 76 amino acid residues in length. In addition, Jacobs, et al. noted that it was not clear that any PS apoprotein derived from the reported precursor protein was present in the surfactant preparations that had been studied clinically by others.

From the foregoing it can be seen that the literature contains multiple nomenclature for what is apparently the same PS apoprotein. Therefore, for ease of discussion, the mature apoprotein derived from the precursor protein described by Glasser, et al. supra, and Jacobs, et al. supra, will be referred to herein generically as "SP18", with the monomeric and dimeric forms being referred to as "SP18 monomer" and "SP18 dimer", respectively, when appropriate.

The canine SP18 precursor has been described by Hawgood, et al, *PNAS USA* 84: 66–70 (1987) and Schilling, et al. International Patent Application WO 86/03408. However, it should be noted that both those studies suffered the same inability to define the mature, biologically active form of SP18 as the Glasser, et al. supra, and Jacobs, et al. supra. studies.

Warr, et al, *PNAS USA* 84: 7915–7919 (1987) describe a cDNA derived sequence of 197 amino acid residues that forms a precursor protein from which a mature LMW apoprotein, they designate as SPS, is formed. Like the studies attempting to describe SP18, Warr, et al. were unable to determine the carboxy terminal residue of the mature

3 protein formed from the precursor protein sequence, and thus were not able to definitively characterize SP5.

Because the amino acid residue sequence of the precursor protein reported by Warr et al. is different from that reported by Glasser, et al. and Jacobs, et al. it therefore appears that the art has determined that natural PS contains at least two LMW apoproteins. However, the biologically active forms of those proteins has remained undetermined.

SUMMARY

The present invention contemplates a polypeptide comprising at least 10 amino acid residues and no more than about 60 amino acid residues, and preferably is in the range of 20–30 residues in length. The polypeptide includes a sequence having alternating hydrophobic and positively charged amino acid residue regions. The polypeptide is represented by the formula $(Z_aU_b)_cZ_d$.

Z is a positively charged amino acid residue, preferably one R or K; U is a hydrophobic amino acid residue, independently selected from the group consisting of V, I, L, C, Y and F. A preferred hydrophobic residue is L.

The average value of a is about 1 to about 5, and is preferably 1.

The average value of b is about 3 to about 20, and is preferably in the range of 4–8, and more preferably is about 4.

The value of c is 1 to 10, and is preferably in the range of 4–8, and more preferably is about 4.

The value of d is 0 to 3, and is preferably 1.

A preferred polypeptide has an amino acid residue sequence represented by the formula:

KLLLLKLLLLKLLLLKLLLLK (SEQ ID NO 1).

The polypeptide, when admixed with a pharmaceutically acceptable phospholipid, forms a synthetic pulmonary surfactant having a surfactant activity greater than the surfactant activity of the phospholipid alone.

A method of treating respiratory distress syndrome comprising administering a therapeutically effective amount of the synthetic pulmonary surfactant is also contemplated.

BRIEF DESCRIPTION OF THE DRAWINGS

FIG. 1 illustrates a 750 nucleotide cDNA sequence (top lines) and deduced amino acid residue sequence (bottom lines). The number to the right of each line-of nucleotides represents the numerical position in the sequence of the nucleotide at the end of each line. The nucleotides are grouped into codons, 15 codons per line, with the amino acid residue coded for by each codon shown in triple letter code directly below the codon. The numerical position of some residues in the amino acid residue sequence encoded by the cDNA is shown below the residues. The amino-terminal amino acid residue of mature human SP18 monomer is Phe (encoded by nucleotides 187–189) and is designated residues number 1. The carboxy-terminal amino acid residue is Asp at residue position 81 (encoded by nucleotides 427–429). A structural gene encoding mature SP18 monomer therefore contains 81 codons and has a nucleotide sequence that corresponds to nucleotides 187–429.

4

Figure 3:
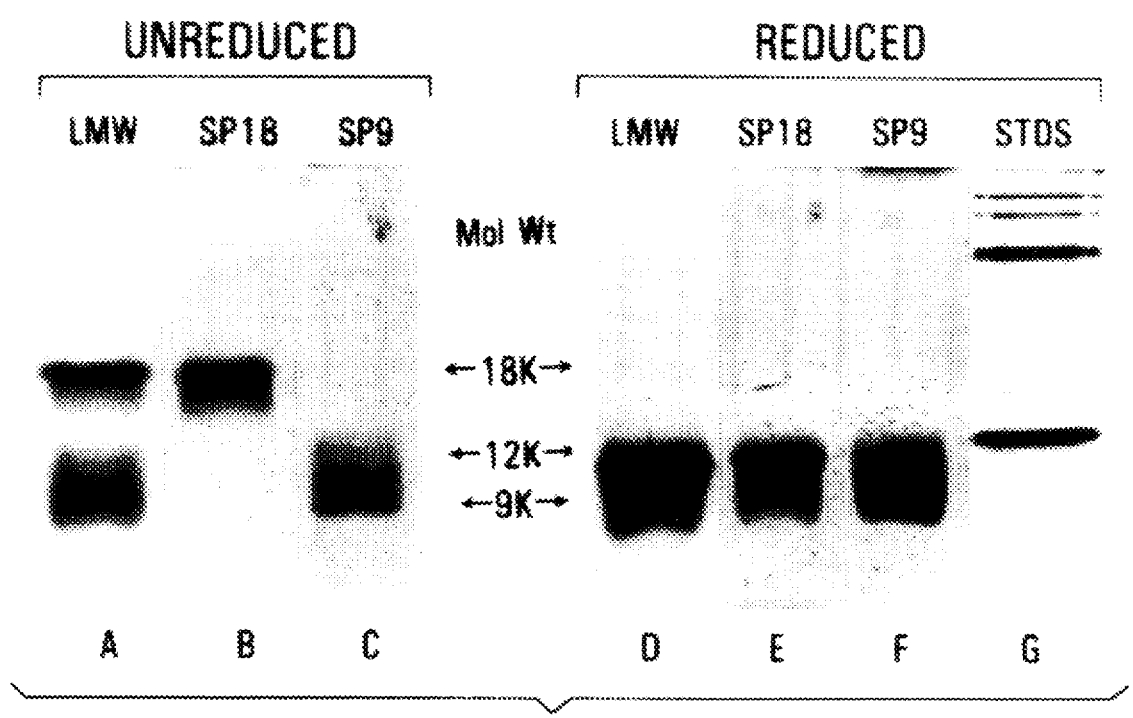

FIG. 3 illustrates a Silver-stained SDS-PAGE of low molecular weight (LMW) PS apoproteins. Lanes A and D show a sample after silicic acid or Sephadex LH-20 chromatography; both LMW proteins are present. Lanes B, C, E and F show the resolution of SP18 (lanes B and E) and SP9 (lanes C and F) following chromatography on Sephadex LH-60. Molecular weight standards are shown in lane G. Lanes A–C are unreduced samples, lanes D–F contain identical samples reduced with β-mercaptoethanol prior to electrophoresis.

Figure 4A:
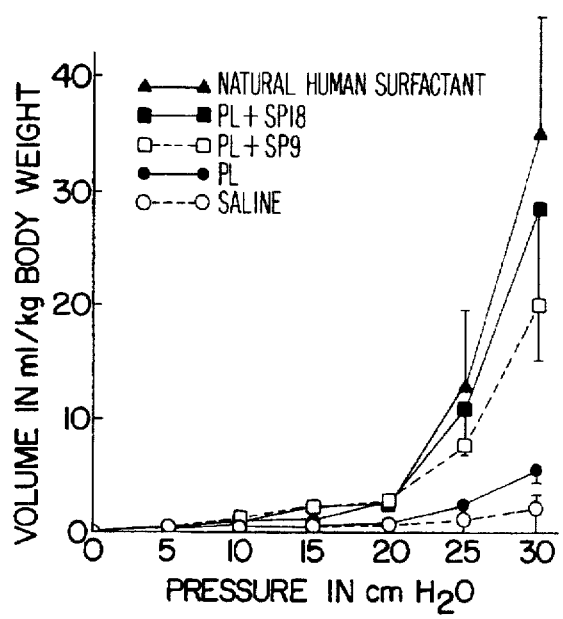
Figure 4B:
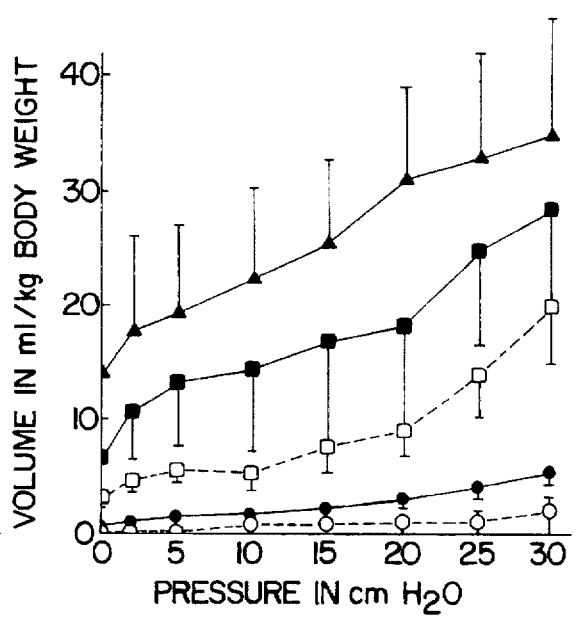
Figure 5A:
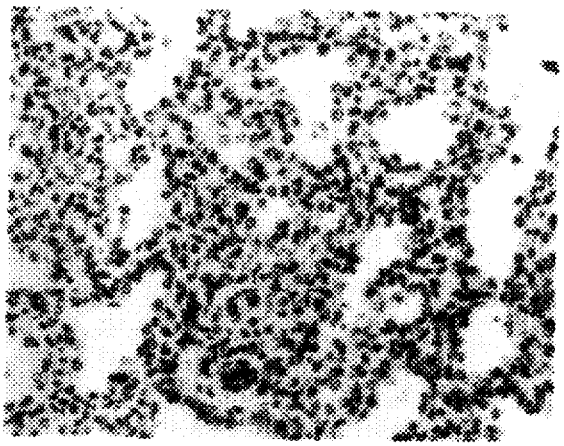
Figure 5B:
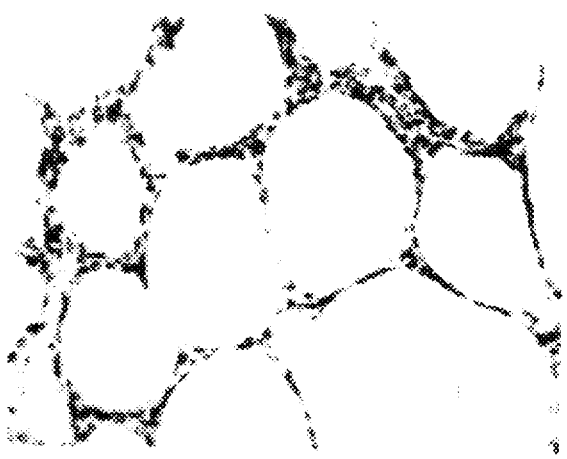
Figure 5C:
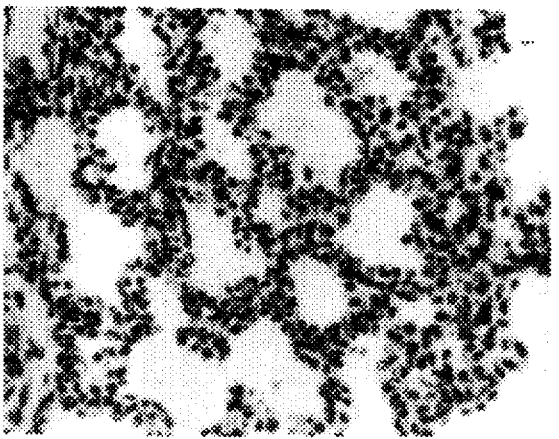
Figure 5D:
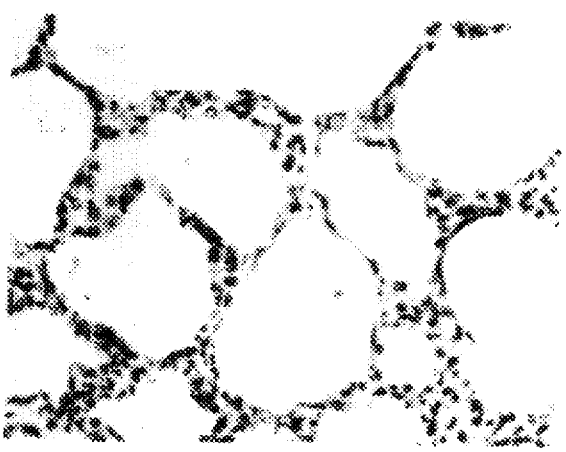

FIGS. 4A and 4B, respectively, illustrate inflation and deflation pressure/volume curves of fetal rabbit lungs 30 min after intratracheal instillation of 100 μl of saline (open circles), 2 mg phospholipids (PL) DPPC:PG, 3:1 (closed circles), PL+10 μg SP9 (open squares) PL+10 μg SP18 (closed squares), or 2 mg natural human surfactant (closed triangles). Data are expressed as the mean of 4 animals±one standard deviation.

FIGS. 5A, 5B, 5C, and 5D illustrate fetal rabbit lung tissue samples (×125 magnification, hematoxylin-eosin stain) following treatment with saline (A), natural human surfactant (B), phospholipids DPPC:PG (C) or phospholipids plus LMW apoproteins (SP9+SP18) (D).

Figure 6:
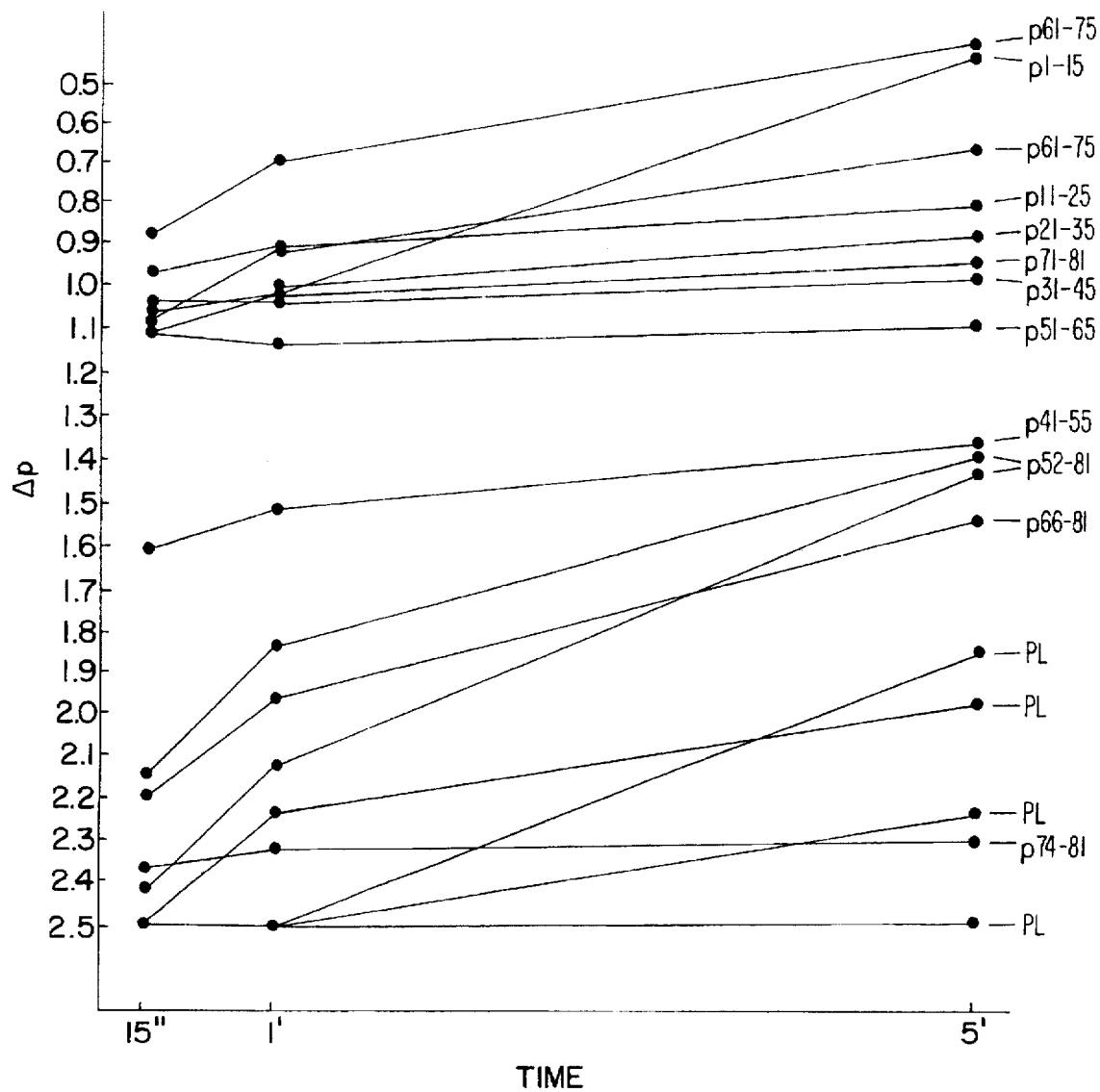

FIG. 6 illustrates the surfactant activity of exemplary polypeptide-containing synthetic surfactants of the present invention. Surfactant activity was determined by measuring the pressure gradient across an air/liquid interface using the pulsating bubble technique. The pressure gradient (ΔP) across the surface of the bubble is the absolute value of the pressure recorded in centimeters of $H_2O$. The results obtained for each synthetic pulmonary surfactant are identified by the polypeptide in the surfactant. Results obtain for surfactants consisting of phospholipid alone (i.e., with no peptide or protein admixed therewith) are identified as PL. The results obtained using a control peptide having only 8 amino acid residues and having a sequence corresponding to human SP18 monomer residues 74–81 (p74–81) are also shown. The data time points shown were obtained at 15 seconds, 1 minute and 5 minutes.

Figure 7B:
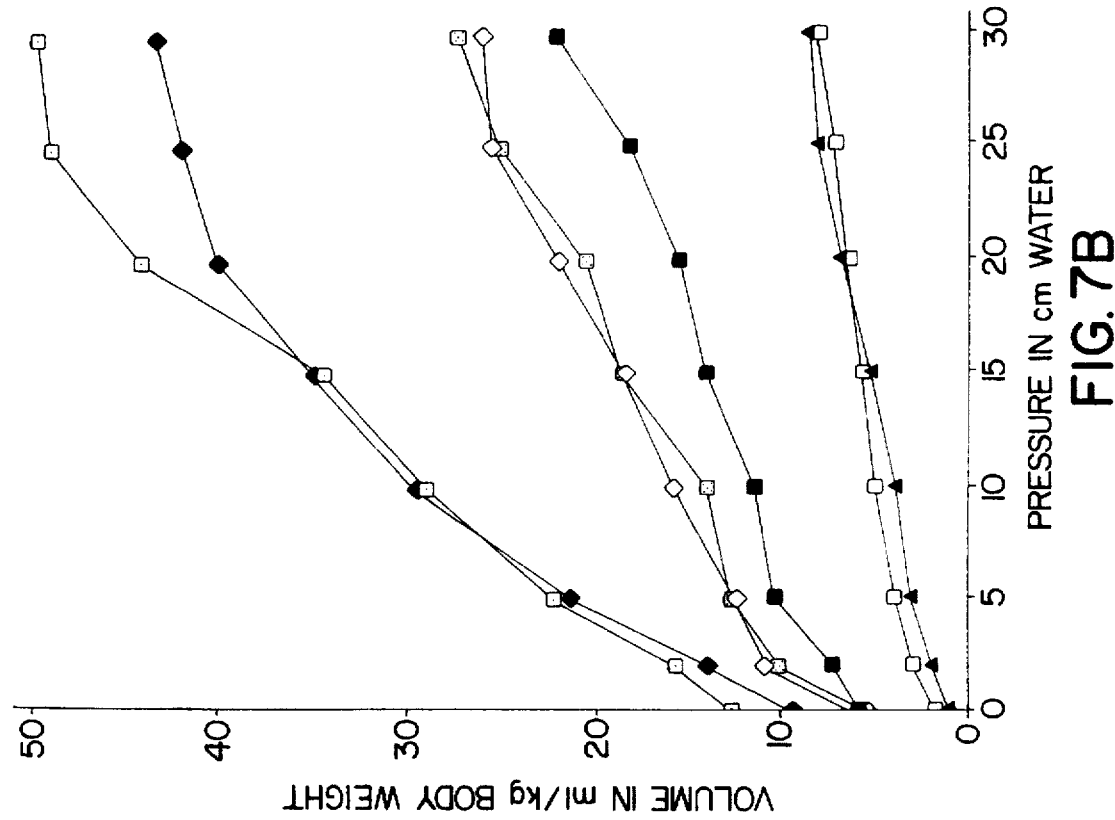
Figure 7A:
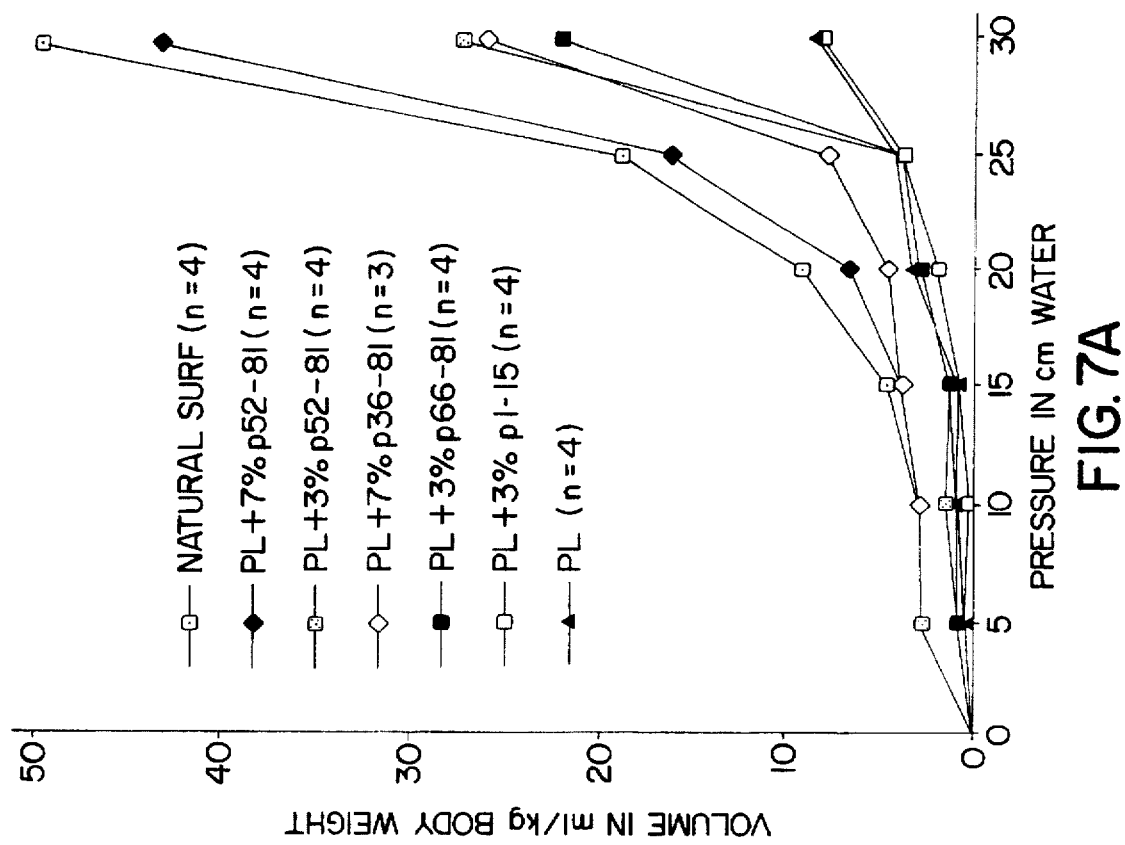

FIGS. 7A and 7B are two graphs that illustrate the results of a static compliance study of exemplary synthetic surfactants of this invention using the fetal rabbit model previously described in Revak, et al. Am. Rev. Respir. Dis. 134: 1258–1256 (1986). Following instillation of a synthetic surfactant or control into the trachea, the rabbit was ventilated for 30 minutes prior to making static compliance measurements. The "x" axis represents the pressure in cm of water, while the "y" axis represents the volume in ml/kg of body weight. The graph in FIG. 7A represents values at inflation and the graph on the right (FIG. 7B) represents deflation values. The results for the following tested surfactants are illustrated: natural surfactant (open square with a dot in the center), phospholipid (PL) with 7% p52–81 (a polypeptide corresponding to residues 52 to 81 of SP18) (closed diamonds); PL with 3% P52–81 (closed squares with white dot in center); PL with 7% p36–81 (open diamonds); PL with 3% p66–81 (closed squares); PL with 3% p1–15 (open squares) and PL control (closed triangles).

Figure 8B:
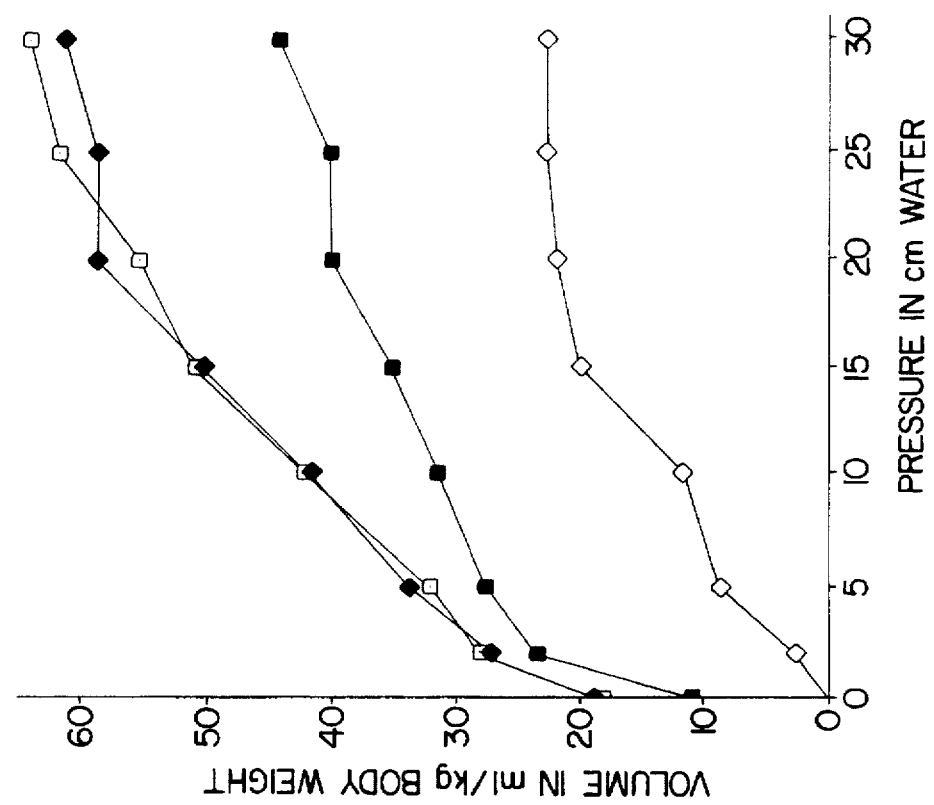
Figure 8A:
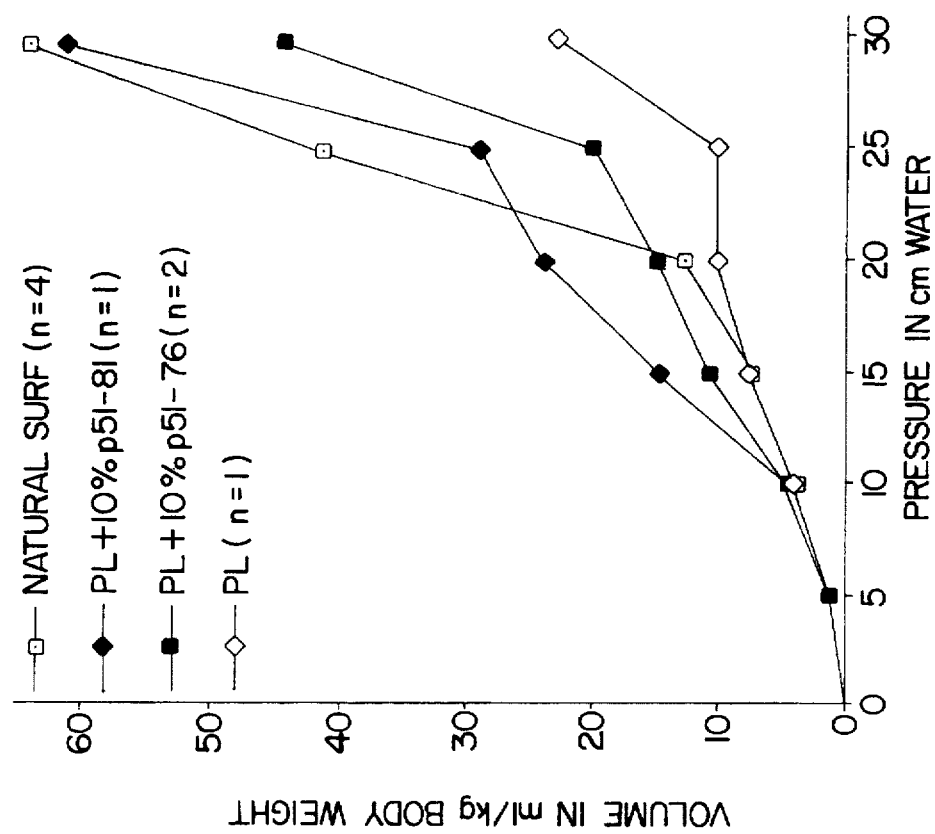

FIGS. 8A and 8B are two graphs that illustrate the results of a static compliance study of exemplary synthetic surfactants of the invention. The procedure was performed as described in FIG. 7 except that a different instillation procedure was used. The "x" and "y" axis and right and left graphs are as described in FIG. 7. The results for the following tested surfactants are illustrated: natural surfactant (open squares); phospholipid (PL) with 10% p51–81 (closed diamonds); PL with 10% p51–76 (closed squares); and PL (closed triangles).

DETAILED DESCRIPTION OF THE INVENTION

A. Definitions

Amino Acid: All amino acid residues identified herein are in the natural L-configuration. In keeping with standard polypeptide nomenclature, *J. Biol. Chem.* 243: 3557–59, (1969), abbreviations for amino acid residues are as shown in the following Table of Correspondence:

| TABLE OF CORRESPONDENCE | | |
|---|---|---|
| SYMBOL | | |
| 1-Letter | 3-Letter | AMINO ACID |
| Y | Tyr | L-tyrosine |
| G | Gly | glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-asparagine |
| C | Cys | L-cysteine |

It should be noted that all amino acid residue sequences are represented herein by formulae whose left to right orientation is in the conventional direction of amino-terminus to carboxy-terminus. Furthermore, it should be noted that a dash at the beginning or end of an amino acid residue sequence indicates a bond to a radical such as H and OH (hydrogen and hydroxyl) at the amino- and carboxy-termini, respectively, or a further sequence of one or more amino acid residues. In addition, it should be noted that a virgule (/) at the right-hand end of a residue sequence indicates that the sequence is continued on the next line.

Polypeptide and Peptide: Polypeptide and peptide are terms used interchangeably herein to designate a linear series of no more than about 60 amino acid residues connected one to the other by peptide bonds between the alpha-amino and carboxy groups of adjacent residues.

Protein: Protein is a term used herein to designate a linear series of greater than about 60 amino acid residues connected one to the other as in a polypeptide.

Nucleotide: a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose it is referred to as a nucleotide.

Base Pair (bp): A partnership of adenine (A) with thymine (T), or of cytosine (C) with guanine (G) in a double stranded DNA molecule.

B. SP18 Monomer-Containing Compositions

The present invention contemplates a SP18 monomer-containing composition (subject protein composition) wherein the SP18 monomer is present in either substantially isolated or substantially pure form. By "isolated" is meant that SP18 monomer and SP18 dimer are present as part of a composition free of other alveolar surfactant proteins.

By "substantially pure" is meant that SP18 monomer is present as part of a composition free of other alveolar surfactant proteins and wherein less than 20 percent, preferably less than 10 percent and more preferably less than 5 percent, of the SP18 monomer present is in homodimeric form, i.e., present as part of SP18 dimer.

Preferably, a SP18 monomer-containing composition of the present invention contains human SP18 monomer. More preferably, a SP18 monomer-containing composition contains SP18 monomer having an amino acid residue sequence corresponding to the amino acid residue sequence shown in FIG. 1 from about residue position 1 to at least about residue position 75, preferably to at least about position 81. More preferably, a SP18 monomer used to form a subject protein composition corresponds in sequence to the sequence shown in FIG. 1 from residue position 1 to residue position 81.

Preferably, the amino acid residue sequence of a SP18 monomer in a subject SP18 monomer-containing composition corresponds to the sequence of a native SP18 monomer. However, it should be understood that a SP18 monomer used to form a protein composition of the present invention need not be identical to the amino acid residue sequence of a native SP18 monomer, but may be subject to various changes, such as those described hereinbelow for a polypeptide of this invention, so long as such modifications do not destroy surfactant activity. Such modified protein can be produced, as is well known in the art, through, for example, genomic site-directed mutagenesis.

"Surfactant activity" for a protein or polypeptide is defined as the ability, when combined with lipids, either alone or in combination with other proteins, to exhibit activity in the in vivo assay of Robertson, *Lung* 158: 57–68 (1980). In this assay, the sample to be assessed is administered through an endotracheal tube to fetal rabbits or lambs delivered prematurely by Caesarian section. (These "preemies" lack their own PS, and are supported on a ventilator.) Measurements of lung compliance, blood gases and ventilator pressure provide indices of activity. Preliminary assessment of activity may also be made by an in vitro assay, for example that of King, et al, *Am. J. Physiol.* 223: 715–726 (1972), or that illustrated below which utilizes a measurement of surface tension at a air-water interface when a protein or polypeptide is admixed with a phospholipid.

C. Nucleic Acid Segments

In living organisms, the amino acid residue sequence of a protein or polypeptide is directly related via the genetic code to the deoxyribonucleic acid (DNA) sequence of the structural gene that codes for the protein. Thus, a structural gene can be defined in terms of the amino acid residue sequence, i.e., protein or polypeptide, for which it codes.

An important and well known feature of the genetic code is its redundancy. That is, for most of the amino acids used to make proteins, more than one coding nucleotide triplet (codon) can code for or designate a particular amino acid residue. Therefore, a number of different nucleotide sequences may code for a particular amino acid residue sequence. Such nucleotide sequences are considered functionally equivalent since they can result in the production of the same amino acid residue sequence in all organisms. Occasionally, a methylated variant of a purine or pyrimidine may be incorporated into a given nucleotide sequence. However, such methylations do not affect the coding relationship in any way.

A DNA segment of the present invention is characterized as consisting essentially of a DNA sequence that encodes a SP18 monomer, preferably human SP18 monomer. That is, a DNA segment of the present invention forms a structural gene capable of expressing a SP18 monomer. While the codons of the DNA segment need not be collinear with the amino acid residue sequence of SP18 monomer because of the presence of an intron, it is preferred that the structural gene be capable of expressing SP18 monomer in mature form, i.e., without the need for post-translational proteolytic processing. Preferably, the gene is present as an uninterrupted linear series of codons where each codon codes for an amino acid residue found in a SP18 monomer, i.e., a gene containing no introns.

Thus, a DNA segment consisting essentially of the sequence shown in FIG. 1 from about nucleotide position 187 to about nucleotide position 426, preferably to about nucleotide position 429, and capable of expressing SP18 monomer, constitutes one preferred embodiment of the present invention.

DNA segments that encode SP18 monomer can easily be synthesized by chemical techniques, for example, the phosphotriester method of Matteuccci, et al, *J. Am. Chem. Soc.* 103: 3185 (1981). Of course, by chemically synthesizing the coding sequence, any desired modifications can be made simply by substituting the appropriate bases for those encoding the native amino acid residue sequence.

Also contemplated by the present invention are ribonucleic acid (RNA) equivalents of the above described DNA segments.

D. Recombinant Nucleic Acid Molecules

The recombinant nucleic acid molecules of the present invention can be produced by operatively linking a vector to a nucleic acid segment of the present invention.

As used herein, the phase "operatively linked" means that the subject nucleic acid segment is attached to the vector so that expression of the structural gene formed by the segment is under the control of the vector.

As used herein, the term "vector" refers to a nucleic acid molecule capable of replication in a cell and to which another nucleic acid segment can be operatively linked so as to bring about replication of the attached segment. Vectors capable of directing the expression of a structural gene coding for SP18 monomer are referred to herein as "expression vectors." Thus, a recombinant nucleic acid molecule (rDNA or rRNA) is a hybrid molecule comprising at least two nucleotide sequences not normally found together in nature.

The choice of vector to which a nucleic acid segment of the present invention is operatively linked depends directly, as is well known in the art, on the functional properties desired, e.g., protein expression, and the host cell to be transformed, these being limitations inherent in the art of constructing recombinant nucleic acid molecules. However, a vector contemplated by the present invention is at least capable of directing the replication, and preferably also expression, of SP18 monomer structural gene included in a nucleic acid segment to which it is operatively linked.

In preferred embodiments, a vector contemplated by the present invention includes a procaryotic replicon, i.e., a DNA sequence having the ability to direct autonomous replication and maintenance of an rDNA molecule extrachromosomally in a procaryotic host cell, such as a bacterial host cell, transformed therewith. Such replicons are well known in the art. In addition, those embodiments that include a procaryotic replicon also include a gene whose expression confers drug resistance to a bacterial host transformed therewith. Typical bacterial drug resistance genes are those that confer resistance to ampicillin or tetracycline.

Those vectors that include a procaryotic replicon can also include a procaryotic promoter capable of directing the expression (transcription and translation) of a SP18 monomer gene in a bacterial host cell, such as *E. coli*, transformed therewith. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Typical of such vector plasmids are pUC8, pUC9, pBR322 and pBR329 available from Biorad Laboratories, (Richmond, Calif.) and pPL and pKK223 available from Pharmacia, Piscataway, N.J.

Expression vectors compatible with eucaryotic cells, preferably those compatible with vertebrate cells, can also be used to form an rDNA molecule of the present invention. Eucaryotic cell expression vectors are well known in the art and are available from several commercial sources. Typically, such vectors are provided containing convenient restriction sites for insertion of the desired DNA segment. Typical of such vectors are pSVL and pKSV-10 (Pharmacia), pBPV-1/pML2d (International Biotechnologies, Inc.), and pTDT1 (ATCC, #31255).

In preferred embodiments, a eucaryotic cell expression vector used to construct an rDNA molecule of the present invention includes a selection marker that is effective in a eucaryotic cell, preferably a drug resistance selection marker. A preferred drug resistance marker is the gene whose expression results in neomycin resistance, i.e., the neomycin phosphotransferase (neo) gene. Southern, et al, *J. Mol. Appl. Genet.* 1: 327–341 (1982).

The use of retroviral expression vectors to form a recombinant nucleic acid molecule of the present invention is also contemplated. As used herein, the term "retroviral expression vector" refers to a nucleic acid molecule that includes a promoter sequence derived from the long terminal repeat (LTR) region of a retrovirus genome.

In preferred embodiments, the expression vector is a retroviral expression vector that is replication-incompetent in eucaryotic cells. The construction and use of retroviral vectors has been described by Sorge, et al, *Mol. Cell. Biol.* 4: 1730–37 (1984).

A variety of methods have been developed to operatively link nucleic acid segments to vectors via complementary cohesive termini. For instance, complementary homopolymer tracts can be added to the nucleic acid segment to be inserted and to a terminal portion of the vector nucleic acid. The vector and nucleic acid segment are then joined by hydrogen bonding between the complementary homopolymeric tails to form a recombinant nucleic acid molecule.

Synthetic linkers containing one or more restriction sites provide an alternative method of joining a nucleic acid segment to vectors. For instance, a DNA segment of the present invention is treated with bacteriophage T4 DNA polymerase or *E. coli* DNA polymerase I, enzymes that remove protruding, 3', single-stranded termini with their 3'-5' exonucleolytic activities and fill in recessed 3' ends with their polymerizing activities. The combination of these activities therefore generates blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease sites are commercially available from a number of sources including International Biotechnologies, Inc., New Haven, Conn.

Also contemplated by the present invention are RNA equivalents of the above described recombinant DNA molecules.

E. Transformed Cells and Cultures

The present invention also relates to a host cell transformed with a recombinant nucleic acid molecule of the present invention, preferably an rDNA capable of expressing an SP18 monomer. The host cell can be either procaryotic or eucaryotic.

"Cells" or "transformed host cells" or "host cells" are often used interchangeably as will be clear from the context. These terms include the immediate subject cell, and, of course, the progeny thereof. It is understood that not all progeny are exactly identical to the parental cell, due to chance mutations or differences in environment. However, such altered progeny are included when the above terms are used.

Bacterial cells are preferred procaryotic host cells and typically are a strain of *E. coli* such as, for example, the *E. coli* strain DH5 available from Bethesda Research Laboratories, Inc., Bethesda, Md. Preferred eucaryotic host cells include yeast and mammalian cells, preferably vertebrate cells such as those from a mouse, rat, monkey or human fibroblastic cell line. Preferred eucaryotic host cells include Chinese hamster ovary (CHO) cells available from the ATCC as CCL61 and NIH Swiss mouse embryo cells NIH/3T3 available from the ATCC as CRL 1658. Transformation of appropriate cell hosts with a recombinant nucleic acid molecule of the present invention is accomplished by well known methods that typically depend on the type of vector used. With regard to transformation of procaryotic host cells, see, for example, Cohen, et al. *Proc. Natl. Acad. Sci. USA* 69: 2110 (1972); and Maniatis, et al, *Molecular Cloning, A Laboratory Manual*, Cold Spring Harbor Laboratory, Cold Spring Harbor, N.Y. (1982). With regard to transformation of vertebrate cells with recombinant nucleic acid molecules containing retroviral vectors, see, for example, Sorge, et al. *Mol. Cell. Biol.* 4: 1730–37 (1984); Graham, et al. *Virol.* 52: 456 (1973); and Wigler, et al, *PNAS USA* 76: 1373–76 (1979).

Successfully transformed cells, i.e., cells that contain a recombinant nucleic acid molecule of the present invention, can be identified by well known techniques. For example, cells resulting from the introduction of an rDNA of the present invention can be cloned to produce monoclonal colonies. Cells from those colonies can be harvested, lysed and their DNA content examined for the presence of the rDNA using a method such as that described by Southern, *J. Mol. Biol.* 98: 503 (1975) or Berent, et al, Biotech. 3: 208 (1985).

In addition to directly assaying for the presence of rDNA, successful transformation can be confirmed by well known immunological methods when the rDNA is capable of directing the expression of an SP18 monomer. For example, cells successfully transformed with an expression vector operatively linked to a DNA segment of the present invention produce proteins displaying SP18 monomer antigenicity. Thus, a sample of a cell culture suspected of containing transformed cells are harvested and assayed for human SP18 using antibodies specific for that antigen, the production and use of such antibodies being well known in the art.

Thus, in addition to the transformed host cells themselves, the present invention also contemplates a culture of those cells, preferably a monoclonal (clonally homogeneous) culture, or a culture derived from a monoclonal culture, in a nutrient medium. Preferably, the culture also contains a protein displaying SP18 monomer antigenicity, and more preferably, biologically active SP18 monomer.

Nutrient media useful for culturing transformed host cells are well known in the art and can be obtained from several commercial sources. In embodiments wherein the host cell is mammalian, a "serum-free" medium is preferably used.

F. Recombinant Methods for Producing SP18

Another aspect of the present invention pertains to a method for producing SP18, preferably human SP18 monomer. The method entails initiating a culture comprising a nutrient medium containing host cells, preferably human cells, transformed with a rDNA molecule of the present invention that is capable of expressing SP18 monomer. The culture is maintained for a time period sufficient for the transformed cells to express SP18 monomer. The expressed protein is then recovered from the culture.

Methods for recovering an expressed protein from a culture are well known in the art and include fractionation of the protein-containing portion of the culture using well known biochemical techniques. For instance, the methods of gel filtration, gel chromatography, ultrafiltration, electrophoresis, ion exchange, affinity chromatography and the like, such as are known for protein fractionations, can be used to isolate the expressed proteins found in the culture. In addition, immunochemical methods, such as immunoaffinity, immunoadsorption and the like can be performed using well known methods.

Also contemplated by the present invention is an SP18 monomer produced by a recombinant nucleic acid method described herein.

G. Polypeptides

A polypeptide of the present invention (subject polypeptide) is characterized by its amino acid residue sequence and novel functional properties. A subject polypeptide when admixed with a pharmaceutically acceptable phospholipid forms a synthetic pulmonary surfactant having a surfactant activity greater than the surfactant activity of the phospholipid alone (as indicated by a lower $\Delta P$ as shown in FIGS. 6, 7 and 8).

As seen in FIG. 1, SP18 has a large hydrophobic region (residues 1 to about 75), followed by a relatively short hydrophilic region at the carboxy terminus (residues 76 to 80, or 81). In referring to amino acid residue numbers of the SP18 sequence, those residues are as illustrated in FIG. 1.

In one embodiment, a subject polypeptide consists essentially of at least about 10, preferably at least 11 amino acid residues, and no more than about 60, more usually fewer than about 35 and preferably fewer than about 25 amino acid residues that correspond to the sequence of SP18 monomer.

Usually, the amino acid sequence of a polypeptide of this invention will correspond to a single group of contiguous residues in the linear sequence of SP18. However, polypeptides that correspond to more than one portion of the SP18 sequence are also contemplated. Usually at least one sequence that corresponds to at least 10, preferably at least 15, contiguous residues of the hydrophobic region of SP18 will be present in the peptide. A plurality of hydrophobic region amino acid sequences may be present.

A subject polypeptide will preferably include as its carboxy terminal sequence at least 5 contiguous residues in the linear sequence of SP18 including residue 80. Thus the polypeptides of this invention may include one or more groups of amino acid residues that correspond to portions of SP18 so that a sequence corresponding to a first group of contiguous residues of the SP18 monomer may be adjacent to a sequence corresponding to a second group of contiguous residues from the same or another portion of the SP18 monomer in the polypeptide sequence. Peptides having two or more sequences that correspond to a single group of contiguous amino acid residues from the linear sequence of SP18 is also contemplated.

Exemplary preferred subject polypeptides corresponding in amino acid residue sequence to human SP18 monomer hydrophobic region are shown in Table 1.

TABLE 1

| Designation[1] | Amino Acid Residue Sequence |
|---|---|
| p1–15 | FPIPLPYCWLCRALI |
| p11–25 | CRALIKRIQAMIPKG |
| p21–35 | MIPKGALAVAVAQVC |
| p31–45 | VAQVCRVVPLVAGGI |
| p41–55 | VAGGICQCLAERYSV |
| p46–76 | CQCLAERYSVILLDTLLGRMLPQLVCRLVLR |
| p51–65 | ERYSVILLDTLLGRM |
| p51–72 | ERYSVILLDTLLGRMLPQLVCR |
| p51–76 | ERYSVILLDTLLGRMLPQLVCRLVLR |
| p54–72 | SVILLDTLLGRMLPQLVCR |
| p54–76 | SVILLDTLLGRMLPQLVCRLVLR |
| p61–75 | LLGRMLPQLVCRLVL |

[1]The designation of each peptide indicates that portion of the amino acid residue sequence of human SP18 monomer, as shown in FIG. 1 to which the peptide sequence corresponds, i.e., it indicates the location of the peptide sequence in the protein sequence.

In preferred embodiments, a subject polypeptide is further characterized as having a carboxy-terminal amino acid residue sequence represented by the formula:

—RLVLRCSMDD$_Z$, wherein Z is an integer having a value of 0 or 1 such that when Z is 0 the D residue to which it is a subscript is absent and when Z is 1 the D residue to which it is a subscript is present. Exemplary preferred "carboxy-terminal polypeptides" are shown in Table 2.

Conservative substitutions are those where one amino acid residue is replaced by another, biologically similar residue. Examples of conservative substitutions include the substitution of one hydrophobic residue such as isoleucine, valine, leucine or methionine for another, or the substitution of one polar residue for another such as between arginine and lysine, between glutamic and aspartic acids or between glutamine and asparagine and the like. The term "conservative substitution" also includes the use of a substituted amino acid in place of an unsubstituted parent amino acid provided that such a polypeptide also displays the requisite binding activity.

In one preferred embodiment, a serine (S) residue is substituted for a cysteine (C) residue, usually at least one of residue positions 71 and 77. Preferably the serine analog has a sequence corresponding to the sequence of residues 51–76 of the SP18 monomer with the substitution at residue 71 or to the sequence of residues 51–81 with serine substitutions at 71 and 77.

When a polypeptide of the present invention has a sequence that is not identical to the sequence of a native SP18 monomer because one or more conservative or non-conservative substitutions have been made, usually no more than about 20 number percent and more usually no more than 10 number percent of the amino acid residues are substituted, except where additional residues have been added at either terminus as for the purpose of providing a "linker" by which the polypeptides of this invention can be conveniently affixed to a label or solid matrix, or carrier. Labels, solid matrices and carriers that can be used with the polypeptides of this invention are described hereinbelow.

Amino acid residue linkers are usually at least one residue and can be 40 or more residues, more often 1 to 10 residues that do not correspond in amino acid sequence to a native SP18 monomer. Typical amino acid residues used for linking are tyrosine, cysteine, lysine, glutamic and aspartic acid, or the like. In addition, a polypeptide sequence of this invention can differ from the natural sequence by the sequence being modified by terminal—NH$_2$ acylation, e.g., acetylation, or thioglycolic acid amidation, terminal-carboxlyamidation, e.g., ammonia, methylamine, etc.

When coupled to a carrier via a linker to form what is known in the art as a carrier-hapten conjugate, a polypeptide of the present invention is capable of inducing antibodies

TABLE 2

| Designation[1] | Amino Acid Residue Sequence |
|---|---|
| p71–81 | CRLVLRCSMDD |
| p66–81 | LPQLVCRLVLRCSMDD |
| p59–81 | DTLLGRMLPQLVCRLVLRCSMDD |
| p52–81 | RYSVILLDTLLGRMLPQLVCRLVLRCSMDD |
| P51–81 | ERYSVILLDTLLGRMLPQLVCRLVLRCSMDD |
| P51–80 | ERYSVILLDTLLGRMLPQLVCRLVLRCSMD |
| p36–81 | RVVPLVAGGICQCLAERYSVILLDTLLGRMLPQLVCRLVLRCSMDD |
| p32–81 | AQVCRVVPLVAGGICQCLAERYSVILLDTLLGRMLPQLVCRLVLRCSMDD |

[1]The designation is the same as in Table 1.

Preferably, a subject polypeptide has an amino acid residue sequence that corresponds to a portion of the sequence shown in FIG. 1. However, it should be understood that a polypeptide of the present invention need not be identical to the amino acid residue sequence of a native SP18 monomer. Therefore, a polypeptide of the present invention can be subject to various changes, such as insertions, deletions and substitutions, either conservative or non-conservative, where such changes provide for certain advantages in their use.

that immunoreact with SP18 monomer. In view of the well established principle of immunologic cross-reactivity, the present invention therefore contemplates antigenically related variants of the polypeptides shown in Tables 1 and 2. An "antigenically related variant" is a polypeptide that includes at least a six amino acid residue sequence portion of a polypeptide from Table 1 or Table 2 and which is capable of inducing antibody molecules that immunoreact with a polypeptide from Table 1 or 2 and an SP18 monomer.

In another embodiment, a polypeptide of this invention has amino acid residue sequence that has a composite hydrophobicity of less than zero, preferably less than or equal to −1, more preferably less than or equal to −2. Determination of the composite hydrophobicity value for a peptide is described in detail in Example 2. These hydrophobic polypeptides perform the function of the hydrophobic region of SP18. In a preferred embodiment, the amino acid sequence mimics the pattern of hydrophobic and hydrophilic residues of SP18.

A preferred hydrophobic polypeptide includes a sequence having alternating hydrophobic and hydrophilic amino acid residue regions and is characterized as having at least 10 amino acid residues represented by the formula: $(Z_aU_b)_cZ_d$.

Z and U are amino acid residues such that at each occurrence, Z and U are independently selected. Z is a hydrophilic amino acid residue, preferably selected from the group consisting of R, D, E and K. U is a hydrophobic amino acid residue, preferably selected from the group consisting of V, I, L, C, Y and F.

"a", "b", "c" and "d" are numbers which indicate the number of hydrophilic or hydrophobic residues. "a" has an average value of about 1 to about 5, preferably about 1 to about 3. "b" has an average value of about 3 to about 20, preferably about 3 to about 12, most preferably about 3 to about 10. "c" is 1 to 10, preferably 2 to 10, most preferably 3 to 6. "d" is 1 to 3, preferably 1 to 2.

By stating that the amino acid residue represented by Z and U is independently selected, it is meant that at each occurrence a residue from the specified group is selected. That is, when "a" is 2, for example, each of the hydrophilic residues represented by Z will be independently selected and thus can include RR, RD, RE, RK, DR, DD, DE, DK, etc. By stating that "a" and "b" have average values, it is meant that although the number of residues within the repeating sequence $(Z_aU_b)$ can vary somewhat within the peptide sequence, the average values of "a" and "b" would be about 1 to about 5 and about 3 to about 20, respectively.

Exemplary preferred polypeptides of the above formula are shown in Table 3A.

TABLE 3A

| Designation[1] | SEQ ID NO | Amino Acid Residue Sequence |
|---|---|---|
| DL4 | | DLLLLDLLLLDLLLLDLLLLD |
| RL4 | | RLLLLRLLLLRLLLLRLLLLR |
| RL8 | | RLLLLLLLLRLLLLLLLLRLL |
| RL7 | | RRLLLLLLLRRLLLLLLLRRL |
| RCL1 | | RLLLLCLLLRLLLLCLLLR |
| RCL2 | | RLLLLCLLLRLLLLCLLLRLL |
| RCL3 | | RLLLLCLLLRLLLLCLLLRLLLLCLLLR |
| KL4 | 1 | KLLLLKLLLLKLLLLKLLLLK |
| KL8 | 2 | KLLLLLLLLKLLLLLLLLKLL |
| KL7 | 3 | KKLLLLLLLKKLLLLLLLKKL |

[1]The designation is an abbreviation for the indicated amino acid residue sequence.

Also contemplated are composite polypeptides of 10 to 60 amino acid residues. A composite polypeptide consists essentially of an amino terminal sequence and a carboxy terminal sequence. The amino terminal sequence has an amino acid sequence of a hydrophobic region polypeptide or a hydrophobic peptide of this invention, preferably hydrophobic polypeptide, as defined in the above formula. The carboxy terminal sequence has the amino acid residue sequence of a subject carboxy terminal peptide.

A polypeptide of the present invention can be synthesized by any techniques that are known to those skilled in the polypeptide art. An excellent summary of the many techniques available may be found in J. M. Steward and J. D. Young, "Solid Phase Peptide Synthesis", W. H. Freeman Co., San Francisco, 1969, and J. Meienhofer, "Hormonal Proteins and Peptides", Vol. 2, p. 46, Academic Press (New York), 1983 for solid phase peptide synthesis, and E. Schroder and K. Kubke, "The Peptides", Vol. 1, Academic Press (New York), 1965 for classical solution synthesis.

In general, these methods comprise the sequential addition of one or more amino acid residues or suitably protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as lysine.

Using a solid phase synthesis as exemplary, the protected or derivatized amino acid is attached to an inert solid support through its unprotected carboxyl or amino group. The protecting group of the amino or carboxyl group is then selectively removed and the next amino acid in the sequence having the complimentary (amino or carboxyl) group suitably protected is admixed and reacted under conditions suitable for forming the amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to afford the final polypeptide.

H. Synthetic Surfactants

Recombinantly produced SP18 and/or a subject polypeptide can be admixed with a pharmaceutically acceptable phospholipid to form a synthetic pulmonary surfactant (PS) useful in the treatment of respiratory distress syndrome.

The phase "pharmaceutically acceptable" refers to molecular entities and compositions that do not produce an allergic or similar untoward reaction when administered to a human.

Phospholipids useful in forming synthetic alveolar surfactants by admixture with protein are well known in the art. See, Notter, et al, Clin. Perinatology 14: 433–79 (1987), for a review of the use of both native and synthetic phospholipids for synthetic surfactants.

In one embodiment, the present invention contemplates a synthetic pulmonary surfactant effective in treating RDS comprising an effective amount of a subject polypeptide admixed with a pharmaceutically acceptable phospholipid. While methods for determining the optimal polypeptide:phospholipid weight ratios for a given polypeptide-phospholipid combination are well known, therapeutically effective ratios are in the range of about 1:5 to about 1:10,000, preferably about 1:100 to about 1:5,000, and more preferably about 1:500 to about 1:1000. In a more preferred embodiment, the polypeptide:phospholipid weight ratio is in the range of about 1:5 to about 1:2,000, preferably about 1:7 to about 1:1,000, and more preferably about 1:10 to about 1:100. Thus, a synthetic pulmonary surfactant of this invention can contain about 50, usually about 80, to almost 100 weight percent lipid and about 50, usually about 20, to less than 1 weight percent polypeptide. Preferably a subject polypeptide is about 1 to about 10 weight percent of the surfactant for polypeptides corresponding to portions of the SP18 sequence and 1:100 for polypeptides corresponding to the entire SP18 monomer.

The lipid portion is preferably about 50 to about 90, more preferably about 50 to about 75, weight percent dipalmitoylphosphatidylcholine (DPPC) with the remainder unsaturated phosphatidyl choline, phosphatidyl glycerol (PG), triacylglycerols, palmitic acid sphingomyelin or admixtures thereof. The synthetic pulmonary surfactant is prepared by admixing a solution of a subject polypeptide with a suspension of liposomes or by admixing the subject polypeptide and lipids directly in the presence of organic solvent. The solvent is then removed by dialysis or evaporation under nitrogen and/or exposure to vacuum.

A subject synthetic pulmonary surfactant is preferably formulated for endotracheal administration, e.g., typically as a liquid suspension, as a dry powder "dust", or as an aerosol. For instance, a synthetic surfactant (polypeptide-lipid micelle) is suspended in a liquid with a pharmaceutically acceptable excipient such as water, saline, dextrose, glycerol and the like. A surfactant-containing therapeutic composition can also contain small amounts of non-toxic auxiliary substances such as pH buffering agents including sodium acetate, sodium phosphate and the like. To prepare a synthetic surfactant in dust form, a synthetic surfactant is prepared as described herein, then lyophilized and recovered as a dry powder.

If it is to be used in aerosol administration, a subject synthetic surfactant is supplied in finely divided form along with an additional surfactant and propellent. Typical surfactants which may be administered are fatty acids and esters. However, it is preferred, in the present case, to utilize the other components of the surfactant complex DPPC and PG. Useful propellants are typically gases at ambient conditions, and are condensed under pressure. Lower alkane and fluorinated alkane, such as Freon, may be used. The aerosol is packaged in a container equipped with a suitable valve so that the ingredients may be maintained under pressure until released.

A synthetic surfactant is administered, as appropriate to the dosage form, by endotracheal tube, by aerosol administration, or by nebulization of the suspension or dust into the inspired gas. Amounts of synthetic PS between about 1.0 and about 400 mg/kg, preferably about 50 mg to about 500 mg/kg, are administered in one dose. For use in newly born infants, one or two administrations are generally sufficient. For adults, sufficient reconstituted complex is administered to produce a $PO_2$ within the normal range (Hallman, et al, *J. Clinical Investigation* 70: 673–682, 1982).

The following examples are intended to illustrate, but not limit, the present invention.

EXAMPLES

Example 1

Isolation and Characterization of Native SP18

A. Methods

1. Purification of LMW apoproteins

Human pulmonary surfactant was isolated from full-term amniotic fluid and applied to a column of DEAE-Sephacel A-50 (Pharmacia, Uppsala, Sweden) using 4 milliliter (ml) packed volume per 200 milligram (mg) surfactant, in a tris-EDTA buffer containing 1% n-octyl-beta-D-glucopyranoside as described by Revak, et al, *Am. Rev. Respir. Dis.* 134: 1258–1265 (1986) and Hallman, et al, *Pediatrics* 71: 473–482 (1983). This particular column and conditions were used in order to isolate the 35,000 dalton apoprotein (for use in other studies) without exposing it to potentially denaturing organic solvents. The void volume, containing the lipids and proteins which did not bind to the column under these conditions, was pooled and extracted with an equal volume of 2:1 chloroform:methanol.

Following centrifugation to separate the phases, the upper phase (water+methanol) was re-extracted with ½ volume chloroform. After centrifugation, the resultant lower organic phase was added to the initial lower phase and evaporated to dryness under a stream of nitrogen. This extract, which contained 100–180 mg phospholipid, LMW apoproteins, and octylglucopyranoside, was redissolved in 2.5 ml of chloroform:methanol, 2:1.

Following the method of Takahashi, et al, *Biochem. Biophys. Res. Comm.* 135: 527–532 (1986), which was found to afford a good separation of octylglucopyranoside from the LMW proteins and phospholipids, a glass column 2.5 cm in diameter was packed at 4° to a height of 38 cm with Sephadex LH-20 (Pharmacia, Uppsala, Sweden) in 2:1 chloroform: methanol. The sample was loaded and 2 ml fractions collected as chloroform:methanol, 2:1, was run through at a flow rate of 8.5 ml/hr. Phospholipids eluted after 40 ml of buffer had passed through the column. Octylglucopyranoside appeared at the 56–116 ml region.

The phospholipid region was pooled, dried under nitrogen, and redissolved in 1 ml chloroform. A silicic acid column was prepared by packing 9 ml of Bio-Sil HA (BioRad, Richmond, Calif.) in chloroform in a glass column at room temperature. The sample (which contained approximately 50 mg phospholipid) was applied and washed with 11 ml chloroform. A linear gradient of increasing methanol was established using an equal weight of chloroform and methanol (38.8 g, 26.5 ml chloroform and 50 ml methanol). Fractions of 2 ml were collected as the gradient was applied to the column. FIG. 1 shows the protein and phospholipid profiles obtained.

Phospholipid analyses showed a small peak in fractions 17–20 and a major peak after fraction 30. The Pierce BCA protein assay was positive in fractions 12–19 and 28–33, but it should be noted that the latter peak is likely to be due to the phospholipid present in this region. Electrophoresis in sodium dodecyl sulfate polyacrylamide gels showed the LMW apoproteins were present in fractions 13–19 with some separation occurring between SP9 and SP18.

Alternatively, a method devised by Hawgood, et al, *Proc. Natl. Acad. Sci.* 85: 66–70 (1987) employing a butanol extraction of PS followed by chromatography of Sephadex LH-20 in an acidified chloroform/methanol buffer, can be used to isolate the LMW apoprotein mixture. For some studies, a separation of the two LMW apoproteins was effected using Sephadex LH-60. A glass column of 1 cm diameter was packed to 40 cm with Sephadex LH-60 (Pharmacia, Uppsala, Sweden) in chloroform/methanol, 1:1, containing 5% 0.1N HCl. A flow rate of 1–2 ml/hr was used. A mixture of the LMW apoproteins containing about 200–700 micrograms (μg) of protein from either the Bio-Sil HA column or the LH-20 column described by Hawgood, et al, *Proc. Natl. Acad. Sci.* 85: 66–70 (1987), in a volume of 0.5 ml buffer, was applied to the top of the column and fractions of 0.5 ml were collected. Typically, SP18 protein eluted in fractions 16–19 and SP9 in fractions 24–29. Appropriate fractions were pooled and dried in glass tubes under nitrogen. A brief period of lyophilization ensured complete removal of the HCl. Proteins were re-solubilized in methanol prior to use.

2. SDS-Gel Electrophoresis

Gel electrophoresis in 16% polyacrylamide was performed in the presence of sodium dodecyl sulfate (SDS-PAGE) according to the method of Laemmli, *Nature* 227: 680–685 (1970), using 3×7 cm minislab gels. 1% β-mercaptoethanol was added to samples where indicated as a disulfide reducing agent. Following electrophoresis, the gels were fixed overnight in 50% methanol +12% acetic acid, washed in water for 2 hours, and silver-stained according to the method of Wray, et al, *Anal. Biochem.* 118: 197–203 (1981).

3. Octylglucopyranoside Assay

An assay for the quantitation of n-octyl-beta-D-glucopyranoside, based on the anthrone method of Spiro, Methods Enzymol. 8: 3–5 (1966) has been described previously by Revak, et al, *Am. Rev. Respir. Dis.* 134: 1258–1265 (1986).

4. Protein Determinations

Organic samples containing up to 5 μg protein were dried in 12×75 mm glass tubes under nitrogen. Fifteen microliters (μl) of 1% SDS in $H_2O$ and 300 μl BCA Protein Assay Reagent (Pierce Chemical Co., Rockford, Ill.) were admixed with the protein in each tube. Tubes were covered and incubated at 60° C. for 30 min. After cooling, the samples were transferred to a 96-well flat-bottom polystyrene microtiter plate and $OD_{550}$ measured. Bovine serum albumin was used as a standard. It should be noted that some phospholipids will react in the BCA protein assay making protein quantitations inaccurate when lipid is present (i.e., prior to Bio-Sil HA chromatography). Additionally, once purified, the hydrophobic LMW apoproteins themselves react poorly with the BCA reagents and all quantitations of the isolated proteins were, therefore, based on amino acid compositions.

5. Phospholipids

Dipalmitoylphosphatidylcholine (DPPC, beta, gamma-dipalmitoyl-L-alpha-lecithin) and L-alpha-phosphatidyl-DL-glycerol (PG, derivative of egg lecithin) were purchased from either Calbiochem-Behring (La Jolla, Calif.) or Avanti Polar-Lipids, Inc. (Birmingham, Ala.). DPPC was added to PG in chloroform in a weight ratio of 3:1.

6. Admixture of LMW Apoproteins with Phospholipids

For in vitro assays, a methanol solution containing 4 μg of SP9 or SP18, was added to 400 μg DPPC:PG in chloroform in a 12×75 mm glass tube. Following a brief vortex mixing, the samples were dried under $N_2$. Ninety microliters of water were added to each and the tubes placed in a 37° C. water bath for 15 minutes, with periodic gentle mixing. Isotonicity was restored with the addition of 10 μl of 9% NaCl to each sample prior to assay. For in vivo rabbit studies, 50 μg LMW apoproteins (containing both SP9 and SP18) or 25 μg SP9 or 25 μg SP18 were dried under $N_2$. Five mg of phospholipids (DPPC:PG, 3:1) were added in chloroform. The samples were mixed, dried, and resuspended in 250 μl 100 millimolar (mM) saline containing 1.5 mM $CaCl_2$, to yield a reconstituted surfactant at 20 mg/ml with 0.5–1% protein.

7. Surfactant Activity Assays

In vitro assays of surfactant activity, assessed as its ability to lower the surface tension of a pulsating bubble, and in vivo assays utilizing fetal rabbits, have both been described in detail previously by Revak, et al, *Am. Rev. Respir. Dis.* 134: 1258–1265 (1986).

8. Morphometric Analyses

Fetal rabbit lungs, inflated to 30 cm $H_2O$ and then deflated to 10 cm $H_2O$, were submerged in 10% formalin for 72 hours. Paraffin sections were oriented from apex to base and 5 micron sections taken anterior to posterior. After hematoxylin and eosin staining, 10 fields (100 x) were point-counted from apex to base on multiple sections. Standardized morphometric methods (Weiber, in "Stereological Methods," Vol. I, Academic Press, New York, pp. 33–58, 1979) were used to determine ratios of lung interstitium to air spaces for each treatment group. Intersections of alveolar perimeters were also determined.

9. Phospholipid Phosphorus Assays

Phospholipids were quantitated according to the method of Bartlett, *J. Biol. Chem.* 234: 466–468 (1959).

10. Amino Acid Analysis

Triplicate samples for amino acid compositions were hydrolyzed with HCl at 110° C. for 24 hours, with HCl at 150° C. for 24 hours, or in performic acid at 110° C. for 24 hours followed by HCl hydrolysis at 110° C. for 24 hours. Analyses were performed on a Beckman model 121-M amino acid analyzer (Beckman Instruments, Fullerton, Calif.). Tryptophan was not determined.

11. Amino Acid Sequencing

Vapor-phase protein sequencing was performed on an Applied Biosystems 470A Amino Acid Sequencer (Applied Biosystems, Inc., Foster City, Calif.) with an on-line Model 120A HPLC.

12. Isolation of cDNA Clones for Human SP18

RNA was prepared according to Chirgwin, et al, *Biochemistry* 18: 5294–5299 (1979) from a sample of unaffected adult lung tissue obtained during surgical removal of a neoplastic lesion. Preparation of double stranded cDNA was carried out using standard techniques (Chirgwin et al., supra, and Efstratiadis et al., in "Genetic Engineering", eds. Stelow and Hollaender, Plenum, N.Y., 1: 15–49 (1979) and a library was constructed in lambda NM607 as described by Le Bouc, et al, *F.E.B.S. Letts.* 196: 108–112 (1986). SP18 clones were identified by screening phage plaques with synthetic oligonucleotide probes (Benton, et al, *Science* 196: 180–182 (1977) which were prepared using an Applied Biosystems automated synthesizer and purified by HPLC. Initial candidate clones were obtained using probe TG996 (5'CATTGCCTGTGGTATGGCCTGCCTCC 3') which was derived from the partial nucleotide sequence of a small human surfactant apoprotein cDNA (Schilling et al., International Patent Application WO 86/03408). Larger clones (up to 1.5 kb) were isolated using probe TG1103 (5'TCGAGCAGGATGACGGAGTAGCGCC 3') which was based on the 5' sequence of one of the original clones. The nucleotide sequence of the cDNA clones was determined by the chain termination method (Sanger, et al, *PNAS USA* 74: 5463–5467 (1977) using EcoRI restriction fragments subcloned in an appropriate M13 vector.

B. Results

1. Characteristics of the LMW Apoproteins

Figure 2:
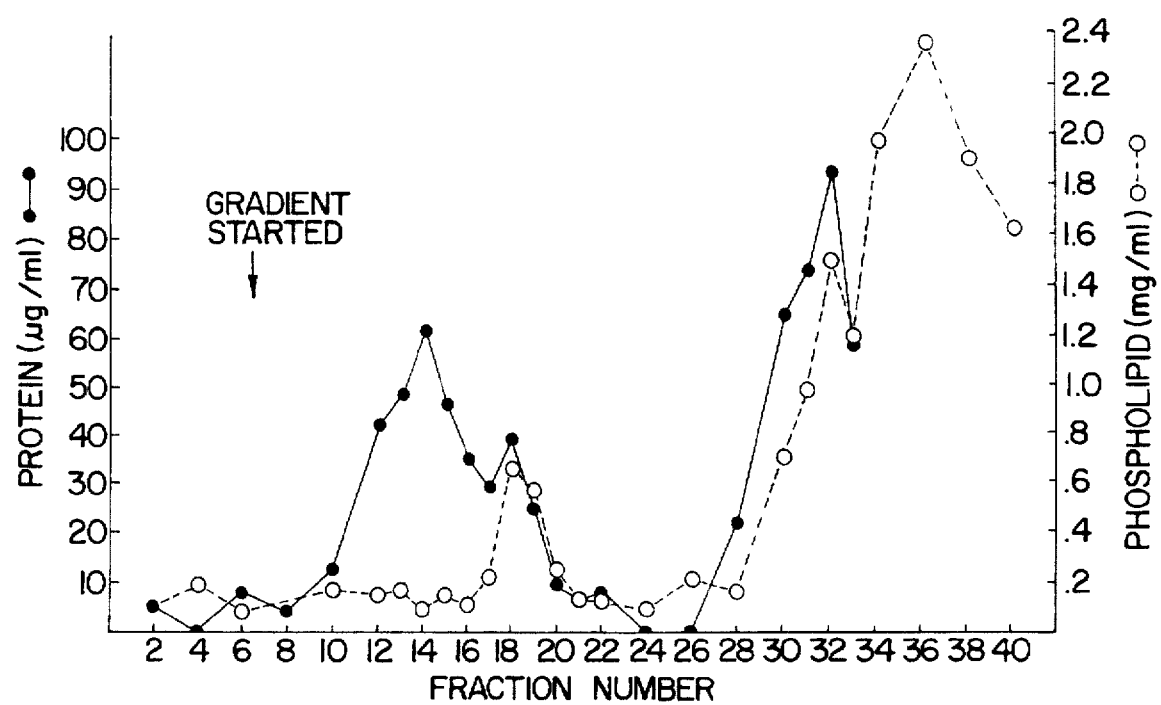
FIG. 2 illustrates the protein elution profile of PS apoproteins from a Bio-Sil HA (silic acid) column. Results of Pierce BCA protein assay (solid line) and phospholipid analyses (broken line) are shown for selected fractions. Two milliliters (ml) were collected per fraction. Positive protein assay in fractions 28 to 33 is due to the presence of phospholipids.

The LMW apoproteins isolated from human amniotic fluid appeared after silicic acid chromatography, or after the Sephadex LH-20 column chromatography FIG. 2 described by Hawgood, et al, *PNAS* 85: 66–70 (1987), as two protein bands in SDS-polyacrylamide gel electrophoresis under non-reducing conditions. The upper band, having an apparent molecular weight of 18,000 daltons is a dimer, and therefore designated SP18 dimer. With the addition of β-mercaptoethanol, SP18 dimer reduced to 9,000 daltons and was designated SP18 monomer (FIG. 3). The other LMW apoprotein, designated SP9, appears as a diffuse band between 9 and 12,000 daltons in the presence or absence of reducing agents. SP9 was separated from SP18 dimer and SP18 monomer by chromatography on Sephadex LH-60. The resultant purified proteins are shown in FIG. 3.

Amino acid compositions were determined for SP18 monomer and SP9. Because of the extremely hydrophobic nature of these proteins, HCl hydrolysis was performed at 150° C. for 24 hours, in addition to the standard 110° C. for 24 hour hydrolysis, and values for valine, leucine, and isoleucine calculated from analyses of the hydrolysates done under the extreme conditions. As shown in Table 3B, both proteins are extremely hydrophobic with high levels of valine and leucine.

TABLE 3B

Amino Acid Composition of Human SP9 and SP18 monomer and a Comparison with the Theoretical Composition of SP18[1]

| Amino Acid | SP9 (mole %) | SP18 (mole %) | SP18[1] (mole %) |
|---|---|---|---|
| Aspartic acid (or Asparagine) | 1.1 | 3.4 | 3.7 |
| Threonine | 0.8 | 1.5 | 1.2 |
| Serine | 1.8 | 2.7 | 2.5 |
| Glutamic acid (or Glutamine) | 1.5 | 6.7 | 6.2 |
| Proline | 8.3 | 7.8 | 7.4 |
| Glycine | 10.6 | 6.1 | 4.9 |
| Alanine | 4.9 | 10.2 | 9.9 |
| Cysteine[2] | 9.1 | 7.2 | 8.6 |
| Valine[3] | 12.2 | 11.7 | 11.1 |
| Methionine | 3.4 | 3.2 | 3.7 |
| Isoleucine[3] | 6.8 | 6.4 | 7.5 |
| Leucine[3] | 22.4 | 17.4 | 17.3 |
| Tyrosine | 0.7 | 2.2 | 2.5 |
| Phenylalanine | 2.6 | 1.5 | 1.2 |
| Histidine | 5.4 | 0.0 | 0.0 |
| Lysine | 4.7 | 3.0 | 2.5 |
| Arginine | 3.9 | 9.0 | 8.6 |
| Tryptophan | N.D.[4] | N.D.[4] | 1.2 |

[1]The theoretical composition is based on sequence data through residue 81.
[2]Cysteine content was determined following performic acid and HCl hydrolyses.
[3]Isoleucine and leucine content were each determined following 24 hour HCl hydrolysis at 150° C.
[4]Tryptophan was not determined.

Amino-terminal sequence analysis of SP18 monomer yielded the following sequence:

NH$_2$-Phe-Pro-Ile-Pro-Leu-Pro-Try-.

Repeated sequencing of the purified SP9 monomer showed multiple peptides, all rich in leucine and containing at least six consecutive valines. NH$_2$-terminal analysis showed phenylalanine, glycine, and isoleucine with the relative amounts of each varying from preparation to preparation.

2. Nucleotide Sequence Analysis of SP18 cDNA

The nucleotide sequence of a SP18 monomer cDNA clone is presented in FIG. 1. The sequence displays 83% homology with the canine SP18 cDNA (Hawgood, et al, PNAS USA 85: 66–70 (1987). A sequence within a large open reading frame was identified which matches perfectly with the amino terminus of SP18 monomer as determined by Edman degradation of the isolated protein (underlined in FIG. 3). This suggests that mature SP18 monomer arises by processing of a larger precursor molecule. In the mature sequence there is a single potential N-glycosylation site (Asn 110), no sites for tyrosine sulfation, and no G-X-Y repeats as found in the 35,000 dalton apoprotein (White, et al, A. Ped. Res. 19: 501–508 (1985)).

The molecular weight of 9000 daltons obtained by SDS-PAGE of reduced SP18 dimer is lower than that predicted for the complete precursor protein sequence with amino terminus NH2-Phe-Pro-Ile-Pro-Leu-Pro-Tyr (19,772 daltons), implying further processing in the region of amino acids 70–90. In support of this, the theoretical amino acid composition (Table I) of a putative 9000 dalton protein comprising residues 1 to 81 compares well with the determined values for purified SP18 monomer. The amino terminal portion of the precursor protein (residues 1 to 81) is alkaline and more hydrophobic than the COOH terminal portion (residues 82 to 181): the Kyte-Doolittle index for residues 1 to 81 is 9100 (pI 8.6) and is −3000 (pI 5.91) for residues 82 to 181 (Kyte, et al, J. Pediatrics 100: 619–622 (1982)). The amino terminus (residues 1 to 81) is, as in the canine sequence (Hawgood, et al, PNAS 85: 66–70 (1987)), composed of three hydrophobic domains: residues 1 to 11, 22 to 49 and 53 to 74. These are interspersed with a charged domain (residues 12 to 21) and two hydrophilic and charged stretches (residues 47 to 54 and 72 to 81).

3. Reconstitution of Surfactant Activity with LMW Apoproteins

Samples were prepared containing 400 µg/100 µl phospholipids (DPPC:PG, 3:1 by weight), phospholipids plus 4 µg SP9, or phospholipids plus 4 µg SP18. Each sample was assayed in the pulsating bubble surfactometer for the ability to lower surface tension. The results are shown in Table 4 as the mean minimal surface tension at 15 sec, 1 minute (min), and 5 min. Natural human surfactant, isolated from term amniotic fluid, diluted to 4 mg/ml is shown for comparison. While neither phospholipids nor LMW apoproteins alone had significant surface-tension lowering capacities, a mixture of phospholipids with either SP9 or SP18 showed significant activity. Recombining the phospholipids with 1% by weight of SP18 lowered the surface tensions measured to levels comparable to those obtained with an equal amount of natural human surfactant (6.3±0.2 dynes/cm for phospholipids+SP18 at 15 sec, 2.0±1.2 dynes/cm for natural surfactant). On an equal weight basis, SP9 lowered surface tension less effectively (16.7±0.8 dynes/cm at 15 sec).

TABLE 4

Minimum Surface Tensions in the Pulsating Bubble[1]

| | 15 sec | 1 min | 5 min |
|---|---|---|---|
| PL[2] | 42.9 ± 1.4 | 41.6 ± 1.6 | 34.9 ± 4.9 |
| PL + SP9[3] | 16.7 ± 0.8 | 14.1 ± 1.2 | 12.2 ± 1.0 |
| PL + SP18[3] | 6.3 ± 0.2 | 5.1 ± 1.0 | 4.9 ± 0.6 |
| natural human surfactant[4] | 2.0 ± 1.2 | 2.4 ± 1.4 | 0.4 ± 0.4 |

[1]Pulsation of 20 cycles/min started 10 sec after bubble formation. All values are in dynes · cm$^{-1}$ and are the average of at least 3 determinations.
[2]Phospholipids DPPC:PG, 3:1, 4 mg/ml
[3]1% by weight compared to phospholipids
[4]diluted to 4 mg/ml In vivo assays of exogenous (synthetic) surfactant activity were performed by instilling into the airways of immature fetal rabbits saline solutions containing Ca$^{++}$ alone or with the addition of phospholipids, phospholipids plus LMW apoproteins, or natural human surfactant. The animals were ventilated for 30 min and then degassed by placement in a bell jar under vacuum. The lungs were then inflated to given pressures and the volume of air required for each pressure was noted. The volumes required for given pressures during deflation from 30 cm H$_2$O were likewise determined. The resulting pressure/volume curves are shown in FIGS. 4A and 4B for animals which received synthetic surfactant made with purified SP9 or SP18 (0.5% by weight compared with total phospholipid concentration) and appropriate control animals. Improved lung compliance is apparent in those animals treated with natural or either synthetic surfactant as compared with those receiving saline or phospholipids with the SP18 appearing more effective than SP9 on an equal weight basis. A similar study was performed using a mixture of SP9 and SP18. The results were almost identical to the phospholipid plus SP18 curve presented in FIGS. 4A and 4B.

Following compliance measurements, the lungs were inflated to 30 cm H$_2$O, deflated back to 10 cm H$_2$O, clamped, excised and fixed in formalin. Thin sections were stained with hematoxylin and eosin and examined microscopically. As shown in FIGS. 5A, 5B, 5C, and 5D, lungs treated with saline (A) or phospholipids (C) appeared atelectatic while those from animals which received natural (B) or reconstituted (D) surfactant showed normal alveolar expansion. Morphometric analyses of the thin sections showed an interstitium to air space ratio of 4.70 for saline treatment and 3.29 for phospholipids alone as compared with 0.498 for natural surfactant and 0.538 for reconstituted surfactant. These data are shown in Table 5 and corroborate the significant (p<0.001; Mann-Whitney U Test) increase in air space seen in FIGS. 5A, 5B, 5C, and 5D. A comparison of alveolar perimeters similarly demonstrated a significantly (p<0.003) greater number of intersections of the alveolar boundaries in saline- or phospholipid-treated fetuses compared to surfactant-treated animals.

TABLE 5

Morphometric Analysis of Airspace Following Fetal Rabbit Treatment

| Tracheal Instillation | Interstitium/Air Space |
|---|---|
| saline | 4.70 |
| phospholipids[1] | 3.29 |
| phospholipids[1] + LMW Apoproteins[2] | 0.538 |
| natural human surfactant[3] | 0.498 |

[1] 2 mg of 3:1 DPPC:PG per animal
[2] 20 μg of LMW apoproteins added to phospholipids
[3] 2 mg per animal C. Discussion This study describes two low molecular weight apoproteins isolated from human amniotic fluid surfactant which can be added to known phospholipids to produce a biologically active pulmonary surfactant. While the proteins in the current study have been designated as SP18 dimer, SP18 monomer and SP9, it is apparent from the recent literature that multiple nomenclature and an assortment of reported molecular weights for LMW PS apoproteins (ranging from 5–18,000 daltons) exist. The apparent differences in physical properties may be explained by a variety of factors including species differences, varying purification and handling techniques, varying determinations of low molecular weights based on standards in SDS-polyacrylamide gels, and potential interference by lipids of low molecular weight protein bands in gels. Comparisons of amino acid compositions and sequences and immunologic analyses using monospecific antibodies will help to sort out the LMW apoproteins.

It is felt that the SP9 protein described herein, giving a diffuse band on SDS-polyacrylamide gels from 9–12,000 daltons under reducing or non-reducing conditions, is probably the same protein as that designated SAP-6 by Whitsett, et al, *Pediatric Research* 20: 744–749 (1986), SP5–8 by Hawgood, et al. *PNAS USA* 85: 66–70 (1987), PSP-6 by Phelps, et al, *Am. Rev. Respir. Dis.* 135: 1112–1117 (1987), and the 5 kDa proteolipid of Takahashi, et al, *Biochem. Biophys Res. Comm.* 135: 527–532 (1986). The extremely hydrophobic nature of this protein is apparent from its amino acid composition (Table 3B) and sequence data, showing at least six consecutive valine residues preceded by a leucine-rich region. The presence of three amino-terminal residues (phenylalanine, glycine, and isoleucine) in the preparations of SP9 derived herein from amniotic fluid surfactant suggests a collection of peptides having an identical sequence but having had one or two residues removed from the amino-terminus. Phelps, et al, *Am. Rev. Respir. Dis.* 135: 1112–1117 (1987) have recently reported a similar finding with bovine PSP-6 apoprotein.

SP18 dimer is comprised of two identical 9000 dalton peptides (but different from the 9000 dalton peptide of SP9) that are disulfide linked. The amino acid composition of SP18 monomer (Table 3B) shows a high number of hydrophobic residues. When unreduced SDS-PAGE were overloaded with SP18 protein, sequentially less intensely staining bands were seen at 36,000 and 56,000 daltons, suggesting oligomeric forms of the protein; upon reduction, only a single 9000 dalton band was seen.

Both SP9 and SP18 dimer apoproteins isolated as described above, could be shown to have biophysical activity following recombination with phospholipids. The addition of 1% by weight of SP18 dimer to the phospholipids DPPC:PG resulted in an immediate increase in surface pressure resulting in surface tensions of less than 10 dynes/cm by 15 sec. The addition of 1% SP9 to DPPC:PG was slightly less effective, lowering surface tensions to 16.7, 14.1, and 12.2 dynes/cm at 15 sec, 1 and 5 min, respectively. Mixtures of both SP18 dimer and SP9 were also effective but further studies will be required to determine whether the combined effect is additive or synergistic.

In vivo studies of reconstituted surfactant using the fetal rabbit model (Schneider, et al, *J. Pediatrics* 100: 619–622; 1982) were performed using mixtures of SP18 dimer and SP9 as well as each protein individually. A marked improvement in lung compliance was seen in animals treated with natural surfactant or reconstituted surfactant prepared with SP18 dimer apoprotein, as compared with those receiving phospholipids alone or saline (FIGS. 4A and 4B). A moderate improvement was seen when SP9 was used. Identical studies using a mixture of SP18 dimer and SP9 to prepare the reconstituted surfactant showed results very similar to those obtained with SP18 dimer alone (solid squares, FIGS. 4A and 4B); however, the exact ratio of SP18 dimer and SP9 in those studies could not be accurately ascertained. FIGS. 5A, 5B, 5C, and 5D show representative microscopic alveolar fields indicating the lack of atelectasis following surfactant instillation.

Suzuki, et al, (*Eur. J. Respir. Dis.* 69: 336–345; 1986) have reported a reduction in surface tension (measured on the Wilhelmy balance or in a pulsating bubble) and a five fold increase in tidal volumes of prematurely-delivered rabbits at insufflation pressures of 25 cm and $H_2O$ when porcine LMW (<15,000 daltons) surfactant apoproteins are added to mixtures of DPPC:PG) at a weight ratio of 5:80:20 (protein:DPPC:PG). Whether one or multiple proteins are present in this system is unclear.

Previous studies using the 35,000 dalton apoprotein (Revak, et al, *Am. Rev. Respir. Dis.* 134: 1258–1265; 1986) also showed moderate reduction in surface tension, similar to that obtained with SP9 in the studies described herein. Clearly, further studies must be done using various combinations and concentrations of SP18, SP9 and the 35,000 dalton apoprotein, as well as $Ca^{++}$ and perhaps various phospholipids to elucidate the interactions between these various components of surfactant and to determine the best conditions for a biologically active exogenous surfactant.

Example 2

In Vitro Assessment of Polypeptide Surfactant Activity

A. Methods

1. Measurement of Surfactant Activity

Measurements of surface pressure across an air-liquid interface (expressed in negative cm of $H_2O$ pressure) at minimal (γmin) bubble radius were determined at various times using the pulsating bubble technique described by Enhorning, *J. Appl. Physiol.* 43: 198–203 (1977).

Briefly, the Enhorning Surfactometer (Surfactometer International, Toronto, Ontario) measures the pressure gradient (ΔP) across a liquid-air interface of a bubble that pulsates at a rate of 20 cycles/min between a maximal (0.55 mm) and minimal (0.4 mm) radius. The bubble, formed in a 37° C., water-enclosed, 20-μl sample chamber, is monitored through a microscopic optic while the pressure changes are recorded on a strip chart recorder calibrated for 0 and −2 cm $H_2O$.

2. Determination of Composite Hydrophobicity Value

The composite hydrophobicity value of each peptide was determined by assigning to each amino acid residue in a peptide its corresponding hydrophilicity value as described in Table 1 of Hopp, et al, *PNAS USA* 78: 3824–3829 (1981), which disclosure is incorporated herein by reference. For a given peptide, the hydrophilicity values were summed, the sum representing the composite hydrophobicity value.

3. Preparation of Synthetic Surfactants

After admixture with solvent, each peptide was combined with phospholipids (DPPC:PG), 3:1 to form a synthetic surfactant according to one of the following methods.

Method A was accomplished by admixing 16 μl of peptide/solvent admixture (40 μg peptide) with 100 μl of chloroform containing 400 μg phospholipids, agitating the admixture for about 10 at 37° C. to form a peptide/phospholipid admixture. Chloroform was removed from the peptide/phospholipid admixture by drying under $N_2$. The synthetic surfactant thus formed was then admixed with 90 μl of $H_2O$ and gently agitated for about 10 minutes at 37° C. Subsequently, 10 μl of 9% NaCl was admixed to the surfactant-containing solution.

Method B was accomplished by first placing 100 μl of chloroform containing 400 μg of phospholipids in a glass tube and removing the chloroform by drying under $N_2$ for about 10 minutes at 37° C. Sixteen μl of peptide/solvent admixture and 74 μl $H_2O$ were admixed with the dried phospholipids, and then gently agitated for about 10 minutes at 37° C. To the synthetic surfactant thus formed was admixed 10 μl of 9% NaCl.

Method C was accomplished by first maintaining the polypeptide-PL admixture at 43° C. for 10 minutes, after which time the solvents were removed from the admixture by drying under $N_2$. When needed, admixtures were further dried by 15 minutes exposure to vacuum to form a dried polypeptide-PL admixture. Water was then admixed with each dried admixture in an amount calculated to equal 90% of the volume necessary to give a final PL concentration of either 5 or 10 mg/ml (as indicated in Table 7) to form a second admixture. This second admixture was maintained for one hour at 43° C. with agitation. Subsequently, a volume of 6% NaCl equal to 10% of the volume necessary to give the desired PL concentration was admixed with the second admixture and the resulting final admixture was maintained for 10 minutes at 43° C. In most cases, the final admixture was subjected to a last step of 3 cycles of freezing and thawing.

B. Results

The synthetic surfactants illustrated in Table 6 were prepared as indicated in the table.

TABLE 6

| Peptide | Solvent | (1) Admixture Formed | (2) Phospholipid Admixture Method | (3) Composite Hydrophobicity Value |
|---|---|---|---|---|
| p1–15 | n-propyl alcohol | suspension | A | −16.7 |
| p11–25 | $H_2O$ | solution | B | +1.7 |
| p21–35 | Chloroform | suspension | A | −9.2 |
| p31–45 | $H_2O$ | solution | B | −9.9 |
| p41–55 | $H_2O$ | solution | B | −5.4 |
| p51–65 | $H_2O$ | suspension | B | −2.2 |
| p61–75 | methanol | suspension | A | −9.9 |
| p71–81 | $H_2O$ | suspension | B | +3.9 |
| p74–81 | $H_2O$ | solution | B | +3.7 |
| p66–81 | methanol:$H_2O$ | suspension | A | −1.0 |
| p52–81 | methanol:$H_2O$ | suspension | A | −6.2 |

(1) Each polypeptide was admixed with the indicated solvent to achieve a concentration of 2.5 μg of peptide per μl of solvent.
(2) The letters indicate the synthetic surfactant preparation method used. Those methods are described above.
(3) The composite hydrophobicity value of each peptide was determined as described above.

Each of the synthetic surfactants indicated in Table 6 were assayed for surfactant activity as evidenced by their ability to reduce surface tension in vitro using the "bubble assay" of Enhorning as described above.

The results of this study, shown in FIG. 6, indicate that a subject polypeptide, when admixed with pharmaceutically acceptable phospholipids, forms a synthetic pulmonary surfactant that has greater surfactant activity than the phospholipids alone, as evidenced by the lower ΔP values. Typically 10% to 80% lower ΔP values were obtained using the polypeptides. It should be noted that the 8 amino acid residue control peptide p74–81, which does not conform to the teachings of the present invention, did not form a synthetic PS having a greater activity than the phospholipid alone, thus indicating that amino acid residue length is a critical feature.

The surfactant activity of additional exemplary polypeptides of this invention was studied using the "bubble assay" as described above. The results of the study are illustrated below in Table 7.

Each polypeptide was admixed with the indicated solvent at a concentration of 2.5 mg of polypeptide per ml of solvent. The resulting admixture was observed to determine whether a solution or a suspension of insoluble polypeptide was formed. Those admixtures forming a suspension were further admixed by water bath sonication for 10 seconds to form a very fine suspension, sufficient for pipetting using glass pipettes.

After admixture with solvent, each peptide was admixed with phospholipids (PL), DPPC:PG, 3:1, in chloroform in a glass tube so that the amount of polypeptide added equaled one-tenth (10% by weight) of the amount of PL added, to form a synthetic surfactant according to either method A, B or C.

Each of the synthetic surfactants was then assayed for surfactant activity as evidenced by their ability to reduce surface tension in vitro in the bubble assay performed as described above. The pressure gradient (ΔP) is a measure of surfactant activity in the polypeptide-PL third admixture which was determined using an Enhorning Surfactometer as described above. Measurements were obtained at time points of 15 seconds (15"), 1 minute (1') and 5 minutes (5') and are expressed as a mean of three independent measurements of the indicated polypeptide-PL admixture. Pressure gradient measurements for comparable samples of PL alone (PL) and natural human surfactants were determined as controls.

The result of this study are shown in Table 7.

TABLE 7

| Peptide | Solvent | (1) Admixture Formed | (2) Phospholipid Admixture Method | (3) Conc. of PL mg/ml | (4) Pressure Gradient 15" | 1' | 5' |
|---|---|---|---|---|---|---|---|
| p1-15 | N-propanol | suspension | A | 4 | 0.94 | 0.82 | 0.48 |
| p36-81 | 50% chloroform 50% methanol | suspension | C+ | 10 | 0.90 | 0.87 | 0.79 |
| p46-76 | 64% chloroform 36% methanol | solution | C+ | 10 | 0.90 | 0.80 | 0.62 |
| p51-72 | 75% chloroform 25% methanol | suspension | C+ | 10 | 1.15 | 0.76 | 0.33 |
| p51-76 | 37% chloroform 63% methanol | solution | C+ | 10 | 0.99 | 0.91 | 0.42 |
| p51-80 | 45% chloroform 55% methanol | solution | C+ | 10 | 0.92 | 0.89 | 0.48 |
| p51-81 | 50% chloroform 50% methanol | suspension | C+ | 10 | 0.94 | 0.86 | 0.64 |
| p52-81 | 67% DMF 33% chloroform | solution | A | 4 | 1.33 | 1.19 | 0.96 |
| p54-72 | 76% chloroform 24% methanol | suspension | C+ | 10 | 1.28 | 0.92 | 0.38 |
| p54-76 | 71% chloroform 24% methanol | suspension | C+ | 10 | 0.92 | 0.82 | 0.23 |
| p59-81 | 68% chloroform 32% methanol | solution | C– | 4 | 1.08 | 1.02 | 0.75 |
| p66-81 | 40% DMF 60% chloroform | suspension | A | 4 | 1.22 | 1.11 | 0.84 |
| p74-81 | water | solution | B | 4 | 2.37 | 2.32 | 2.31 |
| DL4 (31 mer) | 47% chloroform 53% methanol | solution | C– | 4 | 2.00 | 1.80 | 1.30 |
| RL4 | 32% chloroform 68% methanol | solution | C– | 4 | 0.58 | 0.65 | 0.33 |
| RL8 | 19% chloroform 81% methanol | suspension | C+ | 10 | 0.68 | 0.69 | 0.19 |
| RRL7 | 49% chloroform 51% methanol | solution | C– | 4 | 1.65 | 1.25 | 1.00 |
| RCL-1 | 79% chloroform 21% methanol | suspension | C+ | 10 | 0.50 | 0.59 | 0.06 |
| RCL-2 | 67% chloroform 33% methanol | suspension | C+ | 10 | 0.00 | 0.00 | 0.00 |
| RCL-3 | 75% chloroform 25% methanol | suspension | C+ | 10 | 0.55 | 0.51 | 0.33 |
| PL | | | C+ | 10 | >2.50 | >2.50 | 2.33 |
| Natural Human Surfactant | | | | 10 | 1.06 | 0.89 | 0.79 |

(1) Whether the initial admixture of peptide was a solution or a suspension is indicated.
(2) The letters indicate the synthetic surfactant preparation method used. Those methods are described above. A "+" indicates that the final admixture was subjected to a last step of 3 cycles of freezing and thawing. A "–" indicates the step was not performed.
(3) Concentration ("Conc.") of phospholipid (PL) in the final third admixture is indicated in milligrams PL per milliliter admixture (mg/ml).
(4) The pressure gradient is a measure of surfactant activity in the polypeptide-PL final admixture as determined using an Enhorning Surfactometer as described in Example 2. Measurements were obtained at three points of 15 seconds (15"), 1 minute (1') and 5 minutes (5') and are expressed as a mean of 3 independent measurements of the indicated polypeptide-PL admixture. Pressure gradient measurements for comparable samples of PL alone (PL) and natural human surfactant are also shown.

These results indicate that a subject polypeptide, when admixed with pharmaceutically acceptable phospholipids, forms a synthetic pulmonary surfactant that has a greater surfactant activity than the phospholipids alone, as demonstrated by the lower surface pressures obtained.

Example 3

In Vivo Assessment of Synthetic Surfactant Activity

A. Methods

1. Preparation of Synthetic Surfactants

A subject polypeptide was first admixed with solvent as described in Example 2. The resulting admixture was further admixed with phospholipid (PL) so that the amount of polypeptide added was either 3%, 7% or 10% by weight of the amount of PL added as indicated below. The final polypeptide. PL admixture (synthetic surfactant) was formed according to method C using the final freeze thaw step as described in detail in the "Preparation of Synthetic Surfactants" section in Example 2, except that the final admixture had a concentration of 20 mg phospholipid per ml of final admixture.

2. Instillation Protocols

Protocol 1: Fetal rabbits were treated by injection into the trachea of a 0.1 ml solution that contained either a synthetic surfactant prepared in Example 3A or either 2 mg of native surfactant prepared as described in Example 1 or 2 mg PL.

Protocol 2: Synthetic surfactant was instilled in rabbit fetal lung by injection into the trachea from a single syringe of the following three components such that the components exit the syringe in the following order: (1) 0.05 ml air; (2)

0.1 ml of a synthetic surfactant prepared in Example 3A or either 2 mg of PL or 2 mg of native surfactant; and (3) 0.1 ml air.

Protocol 3: From one syringe, a 0.1 ml aliquot of synthetic surfactant prepared as described in Example 3A (or 2 mg of NS or of PL), was instilled into the rabbit trachea as described above, followed by injection of 0.05 ml lactated Ringer's Solution and 0.2 ml air from a second syringe.

Protocol 4: From one syringe, 0.1 ml of a synthetic surfactant prepared as described in Example 3A (or 2 mg of NS or of PL), 0.15 ml air, 0.1 ml saline, and 0.3 ml air were injected into the trachea as described above. Two subsequent aliquots of 0.3 ml air were given.

Protocol 5: Fetal rabbits were treated by injection into the trachea from a single syringe the following four components such that the four components exit the syringe upon injection in the order listed: (1) 0.2 ml solution that contains either a synthetic surfactant prepared in Example 3A or either 4 mg of native surfactant, or 4 mg PL; (2) a 0.15 ml volume of air; (3) a 0.1 ml normal saline solution; and (4) a 0.3 ml volume of air. The above injection was then repeated 15 minutes after the first injection.

Protocol 6: Rabbits were treated as described in Protocol 5, except that two subsequent aliquots of 0.3 ml air were given following the initial instillation and no additional instillation was given at 15 min.

3. Fetal Rabbit Model for Studying Surfactant Activity

The surfactant activity of exemplary polypeptides of this invention was studied using the methods described in detail previously by Revak, et al, *Am. Rev. Respir. Dis.* 134: 1258-1256 (1986), with the exceptions noted hereinbelow.

Twenty-seven day gestation fetal rabbits were delivered by hysterotomy and immediately injected with 0.05 ml Norcuron (Organon, Inc., N.J.) to prevent spontaneous breathing. The fetal rabbits were then weighed and a small cannula was inserted into the trachea by tracheotomy. Synthetic surfactant prepared as described above was then instilled into the fetal rabbit lung by one of the above instillation protocols.

Following instillation the rabbit was placed in a specially designed plethysmograph (containing a Celesco transducer) connected to a ventilator (Baby Bird, Baby Bird Corp., Palm Springs, Calif.) and the instilled lung was ventilated at a rate of 30 cycles per minute with a peak inspiratory pressure of 25 cm $H_2O$, a positive end expiratory pressure of 4 cm $H_2O$ and an inspiratory time of 0.5 seconds. In some studies, dynamic compliance measurements were made at various times throughout the ventilation procedure. In others, static compliance measurements were made following ventilation.

Static compliance measurements were made after 30 minutes of ventilation. The animals were removed from the ventilator and the lungs were degassed at $-20$ cm $H_2O$ in a bell jar under vacuum. Thereafter, the lungs were first inflated and then deflated through a T-connector attached to a tracheostomy tube. The volume of air required to reach static pressures of 5, 10, 15, 20, 25 and 30 cm $H_2O$ was measured during both inflation and deflation phases to generate static pressure to volume curves as a measure of static compliance.

Using the plethysmograph, dynamic compliance measurements were made at various times throughout a 60 minute ventilation period. Computer-assisted data analysis resulted in compliance data expressed as ml of air per cm $H_2O$ per gram of body weight at each time point. Compliance was calculated by the formula below.

$$\text{Compliance} = \frac{\Delta V}{\Delta P}$$

$\Delta P_{tp} = (C)^{-1} \cdot (\Delta V) + (R) \cdot (F)$ $P_{tp}$=transpulmonary pressure C=compliance (elastic component—relates change in volume to pressure)

R=resistance (relates flow to pressure)

F=flow

V=volume=the integral of flow with respect to time

The above equation was solved with a multiple linear regression for C and R. The compliance (C) represents the elastic nature of the lungs and the resistance (R) represents the pressure necessary to overcome the resistance to the flow of gas into and out of the lungs.

B. Results

Static compliance data using instillation protocols 1 and 5 are shown in FIGS. 7 and 8, respectively. Improved lung compliance was seen in all lungs treated with natural surfactant or with the synthetic surfactants tested as compared with those lungs treated with phospholipids (PL) alone, with one exception. The synthetic surfactant prepared using p1-15 (FIGS. 8A and 8E) did not produce improved lung compliance over PL alone when measured by static compliance.

The results of the dynamic compliance studies are illustrated in Table 8.

TABLE 8

Dynamic Compliance in ml air/cm $H_2O$
(g body weight × $10^6$)

| PL | % Peptide Compound To PL | Minutes after Surfactant Instillation | | | | | | Sample[1] Given By Protocol |
|---|---|---|---|---|---|---|---|---|
| | | 10 | 20 | 30 | 40 | 50 | 60 | # |
| PL | | 7 | 8 | 7 | 10 | 11 | 15 | 4 |
| | | 24 | 22 | 23 | 23 | 22 | 20 | 4 |
| | | 15 | 16 | 17 | 18 | 21 | 29 | 4 |
| NS | | 265 | 251 | 168 | 186 | 173 | 147* | 4 |
| | | 418 | 388 | 405 | 288 | 237 | * | 4 |
| | | 155 | 176 | 172 | | 172 | 179 | 4 |
| p36-81 | 5% | | | 255 | | | 146* | 3 |
| | 5% | | | 245 | | | 291 | 3 |
| | 10% | | | 154 | | | 1,162 | 2 |
| | 10% | | | 252 | | | 623 | 2 |
| p52-81 | 5% | | | 517 | | | 226* | 3 |
| | 5% | | | 434 | | | 55* | 3 |
| | 10% | | | 195 | | | 1,243 | 2 |
| | 10% | | | 43 | | | 1,690 | 2 |
| p51-76 | 10% | 33 | 22 | 56 | 87 | 124 | 85 | 4 |
| | 10% | 10 | 11 | 186 | 358 | 141 | 144* | 4 |
| | 10% | 15 | 36 | 109 | 241 | 264 | 301 | 4 |
| p51-80 | 10% | 17 | 41 | 52 | 78 | 99 | 208 | 4 |
| | 10% | 76 | 94 | 149 | 149 | 217 | 308 | 4 |
| | 10% | 23 | 71 | 130 | 156 | 182 | 109* | 4 |

[1]Prior to instillation into the rabbits, these samples were filtered through a 25 micron filter.
*A decrease in compliance with time may indicate the development of pneumothorax.

As shown in Table 8, each of the synthetic surfactants of this invention and natural surfactant improved dynamic compliance values in comparison to phospholipid alone.

C. Discussion

The in vivo compliance studies demonstrate that the use of a number of exemplary synthetic surfactants of this inventions resulted in enhanced compliance in comparison to phospholipid alone for each of the assayed synthetic surfactants. Thus, the proteins and polypeptides of this invention when admixed with pharmaceutically acceptable phospholipids form synthetic surfactants that have greater surfactant activity than phospholipid alone. Use of the synthetic surfactants is advantageous in producing improved compliance values in vivo.

Example 4

Study of Binding of C-Terminal Peptide to Lung Epithelial Cells

A. Methods—Peptide Binding Assay

A peptide having residues 74–80 of SP18 (VLRCSMD) was radiolabeled by the Bolton-Hunter method (Bolton et al., Biochem J. 133: 529–538 1973) with $^{125}$I (New England Nuclear—34.1 moles/ml, 28.0 ng/ml, 75 µCi/ml).

Human pulmonary epithelial cells (human lung carcinoma cell, ATCC reference no. CCL 185, commonly known as A549 cells) were grown to confluence in 6 well tissue culture dishes. The following solutions were used in this study:

PBS/BSA: 10 mM Na Phosphate+0.15M NaCl+0.5% BSA pH 7.4

Lysis Buffer: 1% SDS in water

Solution F: 5 ml PBS/BSA+51.56 µg cold peptide

Solution D: 2.5 ml PBS/BSA+87 µl $^{125}$I-peptide

Solution D1/5: 0.5 ml D+2.0 ml PBS/BSA

Solution D/125: 0.5 ml D1/5+2.0 ml PBS/BSA

Solution E: 2.5 ml PBS/BSA+87 µ$^{125}$I-peptide +20.78 µg cold peptide

Solution E1/5: 0.5 ml E 2.0 ml PBS/BSA

Solution E 1/25: 0.5 ml E1/5+2.0 ml PBS/BSA

Three 6-well plates were pretreated by incubating with 0.5 ml of the following solutions for 15 min. at 22° C. The odd-numbered wells were pretreated with PBS/BSA and the even-numbered wells with solution F. Following removal of the pretreatment solution, the wells were incubated with 0.5 ml of the following solutions at 22° C. for the indicated time while gently rocking the plates.

| Well | Sample | Incubation Time |
| --- | --- | --- |
| 1 | D | 7 minutes |
| 2 | E | 7 minutes |
| 3 | D 1/5 | 7 minutes |
| 4 | E 1/5 | 7 minutes |
| 5 | D 1/25 | 7 minutes |
| 6 | E 1/25 | 7 minutes |
| 7 | D | 30 minutes |
| 8 | E | 30 minutes |
| 9 | D 1/5 | 30 minutes |
| 10 | E 1/5 | 30 minutes |
| 11 | D 1/25 | 30 minutes |
| 12 | E 1/25 | 30 minutes |
| 13 | D | 143 minutes |
| 14 | E | 143 minutes |
| 15 | D 1/5 | 143 minutes |
| 16 | E 1/5 | 143 minutes |
| 17 | D 1/25 | 143 minutes |
| 18 | E 1/25 | 143 minutes |

At the end of the incubation time the supernatant was removed from each well and saved for counting. Each well was washed four times with cold (4° C.) PBS/BSA. The washes were saved for counting. The plate was then brought back to room temperature and 1 ml of lysis buffer was added to each well. The plate was gently shaken until all cells had lysed and come off the plate (3–4 minutes). The solution was removed from each well and counted. A second ml of lysis buffer was added to each well, mixed a few minutes and removed for counting of bound counts. The percent and absolute amounts of counts bound were determined.

Specific counts bound were determined by subtracting the counts bound in wells containing unlabeled (cold) peptide from the corresponding well without cold peptide. The results are illustrated in Table 9, below.

The procedure was repeated with the following changes:

$D_1$=1433 µl PBS/SA+167 µl $^{125}$I-peptide |1.78 pmol/500 µl|

$D_2$=183.3 µl PBS/BSA+366.7 µl $D_1$ |1.19 pmol/500 µl|

$D_3$=275 µl BPS/BSA 275 µl $D_1$ |0.89 pmol/500 µl|

$D_4$=366.7 µl BPS/BSA+183.3 µl $D_1$ |0.59 pmol/500 µl|

$D_5$=458.3 µl BPS/BSA+91.7 µl $D_1$ |0.30 pmol/500 µl|

$D_6$=513.3 µl BPS/BSA+36.7 µl $D_1$ |0.12 pmol/500 µl|

$E_1$=1386.24 µl BPS/BSA+167 µl $^{125}$I-peptide |4.676 µg|+ 46.76 µl cold peptide at 100 µg/ml |4.1676 µl|

$E_2$–$E_6$ Diluted as above for $D_2$–$D_6$.

F=3.398 Ml PBS/BSA+102.29 µl cold peptide at 100 µg/ml

Two six-well plates were washed once with 1 ml PBS/BSA. The odd numbered-wells were pretreated with PBS/BSA and the even-numbered wells with solution F. Following removal of the pretreatment solution, the following solutions were added:

| Well | Sample | Well | Sample |
| --- | --- | --- | --- |
| 1 | $D_1$ | 7 | $D_4$ |
| 2 | $E_1$ | 8 | $E_4$ |
| 3 | $D_2$ | 9 | $D_5$ |
| 4 | $E_2$ | 10 | $E_5$ |
| 5 | $D_3$ | 11 | $D_6$ |
| 6 | $E_3$ | 12 | $E_6$ |

The solutions were incubated for 30 minutes at room temperature with gentle rocking. The supernatants were then removed and saved for counting. Each well was washed 4 times with 0.5 ml of cold PBS/BSA. Washes were saved for counting. 1 ml of 1% SDS was added to each well to solubilize the cells. After 3 minutes all the cells could be seen to have come off the plate. The lysed cell-containing supernatant was counted, together with a second SDS wash of the wells. Total counts and the percentage of counts bound were determined. Specific binding was determined by subtracting the counts bound in wells containing cold peptide from the corresponding well without cold peptide. The results are illustrated in Table 10.

B. Results

The results of the binding studies are illustrated below in Tables 9 and 10.

TABLE 9

| Well | Total CPM | Total CPM Bound | % Bound | Specific Difference | Cts Bound* |
| --- | --- | --- | --- | --- | --- |
| 1 | 1,109,126 | 24,414 | 2.23 | | |
| 2 | 1,087,659 | 17,353 | 1.60 | 0.63% | 6,930 |
| 3 | 223,170 | 4,479 | 2.01 | | |
| 4 | 221,608 | 4,113 | 1.86 | 0.15% | 330 |
| 5 | 45,877 | 828 | 1.80 | | |

TABLE 9-continued

| Well | Total CPM | Total CPM Bound | % Bound | Specific Difference | Cts Bound* |
|---|---|---|---|---|---|
| 6 | 47,731 | 880 | 1.84 | −0.04% | −18 |
| 7 | 1,103,606 | 25,905 | 2.35 | | |
| 8 | 1,152,287 | 19,230 | 1.67 | 0.68% | 7,480 |
| 9 | 227,396 | 4,996 | 2.20 | | |
| 10 | 230,974 | 4,137 | 1.79 | 0.41% | 901 |
| 11 | 47,899 | 1,030 | 2.15 | | |
| 12 | 49,894 | 922 | 1.85 | 0.30% | 132 |
| 13 | 1,151,347 | 10,071 | .87 | | |
| 14 | 1,108,755 | 9,506 | .86 | 0.01% | 110 |
| 15 | 220,340 | 1,692 | .77 | | |
| 16 | 229,253 | 1,800 | .79 | −0.02% | −44 |
| 17 | 46,893 | 407 | .87 | | |
| 18 | 47,426 | 386 | .81 | 0.06% | 26 |

*Corrected to 1,100,000 cpm/undiluted tube.

TABLE 10

| Well | Total CPM | CPM Bound | % Bound | Corrected Difference | p mol |
|---|---|---|---|---|---|
| 1 | 3,070,705 | 66,954 | 2.78 | | |
| 2 | 2,995,775 | 56,055 | 1.87 | 9,390 | 1.78 |
| 3 | 2,029,323 | 39,562 | 1.95 | | |
| 4 | 2,013,557 | 33,573 | 1.67 | 5,723 | 1.19 |
| 5 | 1,436,189 | 26,883 | 1.87 | | |
| 6 | 1,427,731 | 25,073 | 1.76 | 1,755 | .89 |
| 7 | 994,288 | 15,669 | 158 | | |
| 8 | 964,481 | 14,776 | 1.53 | 503 | .59 |
| 9 | 460,317 | 6,513 | 1.41 | | |
| 10 | 479,746 | 6,816 | 1.42 | −52 | .30 |
| 11 | 202,494 | 2,930 | 1.45 | | |
| 12 | 192,990 | 2,806 | 1.45 | 0 | .12 |

*Corrected for 1.78 p mol = 3,033,740 cpm

C. Discussion

As can be seen from the data in Table 9, the study demonstrated that the peptide was binding specifically to the cells as demonstrated by competitive inhibition by unlabeled peptide. However, the cells were not saturated by the amount of labeled peptide used in this study. Additionally, degradation of the peptide was occurring by 143 minutes.

The second study was performed using the 30 minute incubation period and an increased amount of labeled peptide to achieve saturation of the cells. As seen in Table 10, specific binding was again demonstrated. Further, saturation was achieved as demonstrated by leveling-off of the amount of bound counts at high concentration of labeled peptide.

The binding studies thus demonstrate that the C-terminal peptide of this invention binds specifically to lung epithelial cells.

The foregoing specification, including the specific embodiments and examples, is intended to be illustrative of the present invention and is not to be taken as limiting. Numerous other variations and modifications can be effected without departing from the true spirit and scope of the present invention.

We claim:

1. A pulmonary surfactant comprising one or more pharmaceutically acceptable phospholipids admixed with a polypeptide having an amino acid residue sequence represented by the formula KLLLLKLLLLKLLLLKLLLLK (SEQ. ID NO: 1), said polypeptide, thereby forming a pulmonary surfactant having a surfactant activity greater than the surfactant activity of the phospholipid alone, said phospholipid being present in the range of about 50–100 weight percent, in a polypeptide:phospholipid weight ratio in the range of about 1:7 to about 1:1,000.

2. The pulmonary surfactant of claim 1, wherein said phospholipid is selected from the group consisting of:

1,2-dipalmitoyl-sn-glycero-3-phosphocholine (dipalmitoylphosphatidylcholine, DPPC);

phosphatidyl glycerol (PG); and an admixture of DPPC and PG in a weight ratio of about 3:1.

3. The pulmonary surfactant of claim 1, further comprising palmitic acid, wherein said phospholipid comprises about 50–90 weight percent and said palmitic acid comprises the remaining 10–50 weight percent of said surfactant.

4. A method of treating respiratory distress syndrome comprising administering a therapeutically effective amount of a pulmonary surfactant, said surfactant comprising one or more pharmaceutically acceptable phospholipids admixed with a polypeptide having an amino acid residue sequence represented by the formula KLLLLKLLLLKLLLLKLLLLK (SEQ. ID NO: 1), said polypeptide, when admixed with a pharmaceutically acceptable phospholipid, forming a pulmonary surfactant having a surfactant activity greater than the surfactant activity of the phospholipid alone, said phospholipid being present in the range of about 50–100 weight percent, in a polypeptide:phospholipid weight ratio in the range of about 1:7 to about 1:1,000, or in an amount such that it may be administered in a range of about 50 mg/kg to about 500 mg/kg per dose.

5. The method of claim 4, wherein said phospholipid is selected from the group consisting of:

1,2-dipalmitoyl-sn-glycero-3-phosphocholine (dipalmitoylphosphatidylcholine, DPPC);

phosphatidyl glycerol (PG); and an admixture of DPPC and PG in a weight ratio of about 3:1.

6. The method of claim 4, wherein said surfactant further comprises palmitic acid, and wherein said phospholipid comprises about 50–90 weight percent and said palmitic acid comprises the remaining 10–50 weight percent of the lipid portion of said surfactant.

\* \* \* \* \*

UNITED STATES PATENT AND TRADEMARK OFFICE
CERTIFICATE OF CORRECTION

PATENT NO.    : 5,789,381
DATED         : August 4, 1998
INVENTOR(S)   : Cochrane et al.

It is certified that error appears in the above-identified patent and that said Letters Patent is hereby corrected as shown below:

<u>Column 1,</u>
Line 4, insert: -- This invention was made with government support under Grant Nos. HL. 23584 and GM 37696 from the National Institutes of Health and Grant No. N00014-89-K-0029 from the Office of Naval Research. The U.S. government may have certain rights in the invention. --

Signed and Sealed this

Ninth Day of April, 2002

*Attest:*

*Attesting Officer*

JAMES E. ROGAN
*Director of the United States Patent and Trademark Office*

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
      ( A ) LENGTH: 21 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:1:

Lys Leu Leu Leu Leu Lys Leu Leu Leu Leu Lys Leu Leu Leu Leu Lys
1               5                   10                  15

Leu Leu Leu Leu Lys
            20

( 2 ) INFORMATION FOR SEQ ID NO:2:

( i ) SEQUENCE CHARACTERISTICS:
      ( A ) LENGTH: 21 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:2:

Lys Leu Leu Leu Leu Leu Leu Leu Leu Lys Leu Leu Leu Leu Leu Leu
1               5                   10                  15

```
    Leu  Leu  Lys  Leu  Leu
                20
```

(2) INFORMATION FOR SEQ ID NO:3:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO:3:

```
    Lys  Lys  Leu  Leu  Leu  Leu  Leu  Leu  Leu  Lys  Lys  Leu  Leu  Leu  Leu  Leu
    1                  5                            10                           15

Leu  Leu  Lys  Lys  Leu
                20
```